ative Data

| [54] | AMINO ACID ESTERS |
| --- | --- |
| [75] | Inventor: Walfred S. Saari, Lansdale, Pa. |
| [73] | Assignee: Merck & Co., Inc., Rahway, N.J. |
| [21] | Appl. No.: 668,021 |
| [22] | Filed: Mar. 18, 1976 |

Related U.S. Application Data

[60] Division of Ser. No. 482,102, June 25, 1974, Pat. No. 3,983,138, which is a continuation-in-part of Ser. No. 400,609, Sept. 25, 1973, abandoned.

[51] Int. Cl.$^2$ ............... C07D 211/88; A61K 311/445
[52] U.S. Cl. ...................... 260/281 GN; 260/518 R; 560/40
[58] Field of Search ................................. 260/281 GN

[56] References Cited

U.S. PATENT DOCUMENTS 3,988,341  10/1976  Saari et al. ................... 260/281 GN Primary Examiner—Donald G. Daus
Assistant Examiner—Mark L. Berch
Attorney, Agent, or Firm—Daniel T. Szura; Harry E. Westlake, Jr.

[57] ABSTRACT

Derivatives of α-methyl-3,4-dihydroxyphenylalanine which are useful in compositions as anti-hypertensive agents.

10 Claims, No Drawings

AMINO ACID ESTERS

This is a division of copending application Ser. No. 482,102, now U.S. Pat. No. 3,983,138 filed June 25, 1974, which in turn is a continuation-in-part of Ser. No. 400,609, filed Sept. 25, 1973, now abandoned.

The present invention relates to a novel and useful class of compounds and the use of the compounds in the treatment of hypertension. More particularly, it relates to derivatives of α-methyl-3,4-dihydroxyphenylalanine.

It has been suggested in the art that various alanine compounds may be useful in the treatment of hypertension (see U.S. Pat. No. 2,868,818). It is further known in the art that hypertension is preferably treated with L-α-methyl-3,4-dihydroxyphenylalanine since the D-form of the compound is therapeutically inert and only the L-form is therapeutically active. The removal of the D-form thereby lessens toxicity and increases effectiveness (see U.S. Pat. No. 3,344,023 and British Pat. No. 936,074). The L-isomer of α-methyl-3,4-dihydroxyphenylalanine is commonly referred to as L-α-methyldopa or methyldopa. It is still further known in the art that the alkyl esters of L- or DL-α-methyl-3,4-dihydroxyphenylalanine are useful in the emergency treatment of hypertension by parental administration (see U.S. Pat. No. 3,230,143). It has now been found that other esters and derivatives of DL- or L-α-methyl-3,4-dihydroxyphenylalanine having specific structures are also active in the treatment of hypertension thereby giving alternative compounds for such treatment. It has also been found that some of the new compounds have a much higher activity and thus require a lower dosage than the known compounds.

Accordingly, it is an object of the present invention to provide a novel and useful class of compounds which are active in treating hypertension. A further object is to provide a more active group of compounds for the treatment of hypertension. A still further object is to provide a method of producing such compounds. Another object is to provide a method of treatment for hypertension by the use of the new compounds. Another object is to provide a novel and useful composition for the treatment of hypertension. Other objects will become apparent as the description of the invention proceeds.

These objects are accomplished by the present invention which provides a compound of the formula

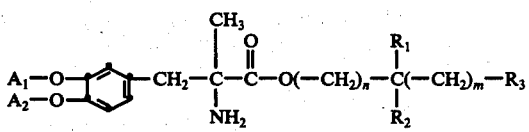

wherein
 $n$ is 0, 1, 2 or 3;
 $m$ is 0, 1, 2 or 3;
 $A_1$ and $A_2$ are individually H or a lower alkanoyl group;
 $R_1$ and $R_2$ are individually H or alkyl of 1 to 3 carbon atoms and;
 $R_3$ is selected from the group consisting of
  A. a monocyclic or bicyclic heterocyclic radical containing from 3 to 12 nuclear carbon atoms and 1 to 2 nuclear hetero atoms selected from N and S with at least one being N, and with each ring in the said heterocyclic radical containing 5 to 6 members and
  B. the radical $X-R_4$ wherein X is —O—, —S— or —NH— and $R_4$ contains up to 21 carbon atoms and is (1) a hydrocarbon radical or (2) an acyl radical of an organic acyclic or monocyclic carboxylic acid containing not more than 1 hetero atom in the ring or a pharmaceutically acceptable acid addition salt thereof.

In a preferred embodiment of the present invention, $n$ and $m$ are 0 or 1, $A_1$ and $A_2$ are H, $R_1$ and $R_2$ are hydrogen or methyl and $R_3$ is the heterocyclic ring

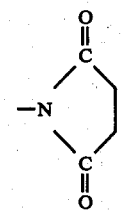

which may be substituted by lower alkyl groups of 1 to 3 carbon atoms, or $R_3$ is —X—$R_4$ where X is —O— or —NH— and $R_4$ is an acyl radical from an alkanoic acid containing 2 to 5 carbon atoms.

The present invention further provides an ester of the L isomer of an amino acid, substantially free of the D isomer, having the formula

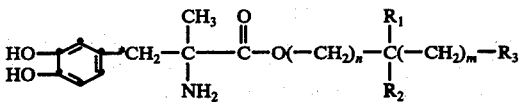

or a pharmaceutically acceptable acid addition salt thereof wherein $n$, $m$, $R_1$, $R_2$ and $R_3$ are as defined above. With regard to the L isomer, it should be noted that the asymmetric carbon atom is the one containing the amino and methyl group in the acid portion of the molecule. It is this portion of the molecule that is referred to as being in the L configuration. Note that the L configuration refers to the stereo configuration and not to the optical rotation through in this case the L stereo configuration is the l or levo form of the optical isomer. However, it should also be noted that in some instances when $R_1$ and $R_2$ are different groups the carbon atom to which they are attached is also an asymmetric carbon atom and can thus exist in either the L or D configuration. As is hereinafter pointed out, both of the isomers of this portion of the compound are active. As is further pointed out, these stereo isomers have been separated but their stereo configuration has not been determined so they are merely designated as the α and β isomer. In any event, both the α and β isomers are active regardless of their stereo configuration.

The present invention still further provides a method of treating hypertension in a hypertensive animal which comprises administering to the animal a therapeutically effective amount of a compound of the formula

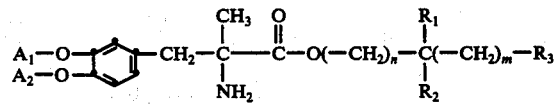

or a pharmaceutically acceptable acid addition salt thereof wherein $n$, $m$, $A_1$, $A_2$, $R_1$, $R_2$ and $R_3$ are as defined above.

In the treatment of hypertension, the compounds of the present invention are generally administered in amounts of from about 0.005 to about 300 mg./kg. of body weight of the animal and preferably from about 0.05 to about 100 mg./kg. In a still more preferred embodiment, the compounds are administered in amounts of from about 0.1 to about 25 mg./kg. of body weight of the animal. In this regard, it should be noted that the dosage must be adjusted depending upon the activity of the compound, the response desired in the reduction of blood pressure and also the weight of the animal. In the ranges given above, the more active compounds would tend to be given at the lower dosages and the less active compounds at the higher dosages.

The present invention also provides a method of treating hypertension in a hypertensive animal which comprises administering to the animal a therapeutically effective amount of an ester of the L isomer of an amino acid, substantially free of the D isomer, having the formula

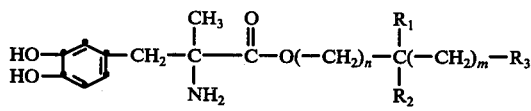

or a pharmaceutically acceptable acid addition salt thereof wherein $n$, $m$, $R_1$, $R_2$ and $R_3$ are as defined above.

When the L isomer of a compound of the present invention is given in the substantial absence of the D isomer, the required dosage of the L isomer is approximately one-half of that of the racemate since the D isomer is therapeutically inactive. However, the compounds of the present invention vary in activity to some degree and thus the racemate of one of the less active compounds of the present invention may require several times the dosage of a more active compound. In general, the compounds will be administered within the above dosages.

The present invention also provides a pharmaceutical composition comprising an inert pharmaceutically acceptable diluent and a compound of the formula

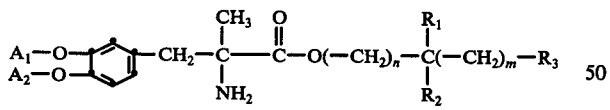

or a pharmaceutically acceptable acid addition salt thereof wherein $n$, $m$, $A_1$, $A_2$, $R_1$, $R_2$ and $R_3$ are as defined above.

In a single dosage form of the composition of the present invention, the active compound is generally present in the composition in amounts of from about 1 mg. to about 2,000 mgs., more preferably about 5 mgs. to about 1,000 mgs. In a still more preferred embodiment, the active compound is present in amounts of from about 10 mgs. to about 500 mgs. The single dosage form of the compound may be administered in a single slow acting dose or it may be administered in several small doses throughout the day, generally 2 to 8 individual dosages.

The present invention also provides a pharmaceutical composition comprising an inert pharmaceutically acceptable diluent and an ester of the L isomer of an amino acid, substantially free of the D isomer, having the formula

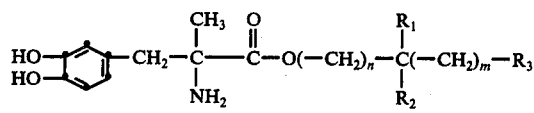

or a pharmaceutically acceptable acid addition salt thereof wherein $n$, $m$, $R_1$, $R_2$ and $R_3$ are as defined above.

As in the method of treatment, reduced dosages of the L isomer substantially free of the D isomer are required as compared to the racemate. However, the difference in activity of various compounds requires the use of different dosages. In some instances, the compounds are many times more active than others and thus the racemate of one may require even less of a dosage than the L isomer of a second. In general, however, the dosages will be within the above ranges.

The present invention further provides a process for preparing a compound of the formula

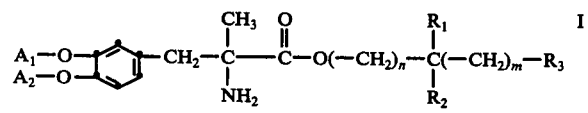

wherein
$n$ is 0, 1, 2 or 3;
$m$ is 0, 1, 2 or 3;
$A_1$ and $A_2$ are individually H or a lower alkanoyl group;
$R_1$ and $R_2$ are individually H or alkyl of 1 to 3 carbon atoms and;
$R_3$ is selected from the group consisting of
  A. a monocyclic or bicyclic heterocyclic radical containing from 3 to 12 nuclear carbon atoms and 1 or 2 nuclear hereto atoms selected from N and S with at least one being N, and with each ring in the said heterocyclic radical containing 5 to 6 members and
  B. the radical $X—R_4$
wherein
  X is —O—, —S— or —NH— and
  $R_4$ contains up to 21 carbon atoms and is (1) a hydrocarbon radical or (2) an acyl radical of an organic acyclic or monocyclic carboxylic acid containing not more than 1 hereto atom in the ring or an acid addition salt thereof which comprises
a. the hydrolysis or reduction of an acid derivative of the formula

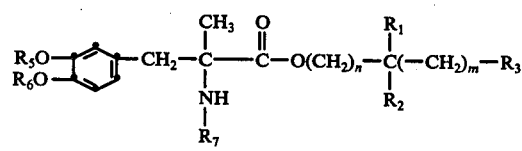

or an acid addition salt thereof wherein $n$, $m$, $R_1$, $R_2$ and $R_3$ are as defined above and $R_5$, $R_6$ and $R_7$ are hydrogen or a blocking group with at least one being a blocking group; or b. the esterification of an acid derivative of the formula

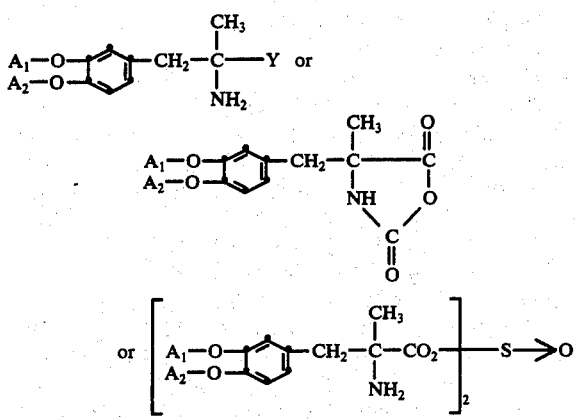

or an acid addition salt thereof with a compound of the formula

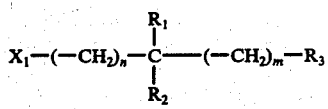

wherein Y is —COOH, —COhalogen or —carboxylic acid salt and $n$, $m$, $A_1$, $A_2$, $R_1$, $R_2$ and $R_3$ are as defined above and $X_1$ is hydroxyl, alkali metal —O—, halogen or a substituted —SO$_3$— group; or c. the reduction of a compound of Formula I wherein $R_3$ contains one or more reducible groups; or d. the reaction of a compound of the formula

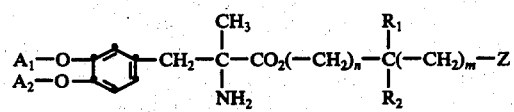

wherein $n$, $m$, $A_1$, $A_2$, $R_1$ and $R_2$ are as given above and Z is —OH, —SH, halogen, substituted —SO$_3$— group or —NH$_2$ with an acylating agent; $R_3$—H or $R_3$—alkali metal wherein $R_3$ is as defined above; or e. the cyclization of a compound of the formula

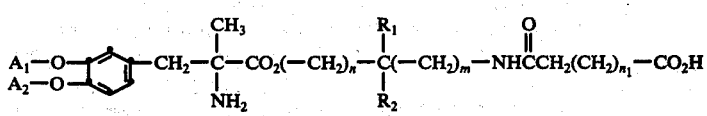

wherein $n_1$ is 1, 2 or 3; $A_1$, $A_2$, $R_1$, $R_2$, $n$ and $m$ are as defined above with an acylating agent and, if desired, separating the stereoisomers by (1) fractional crystallization of one stereoisomer from solution or (2) forming diastereomers with an optically active acid and crystallizing one of the diastereomers from the solution.

The present invention further provides a process for preparing a compound of the formula

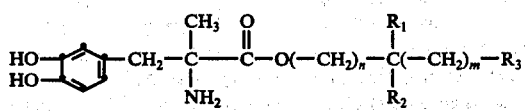

or an acid addition salt thereof wherein $n$, $m$, $R_1$, $R_2$ and $R_3$ are as defined above which comprises the hydrolysis or reduction of an acid derivative of the formula

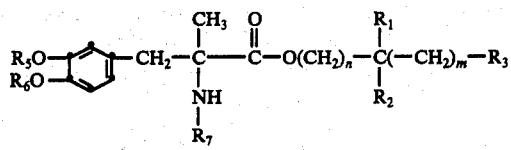

or an acid addition salt thereof wherein $R_5$, $R_6$ and $R_7$ are individually hydrogen or a blocking group with at least one being a blocking group. The hydrolysis or reduction is carried out under conventional conditions.

The present invention further provides a process for preparing a compound of the formula

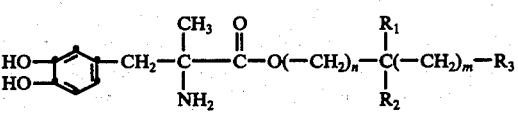

or an acid addition salt thereof wherein $n$, $m$, $R_1$, $R_2$ and $R_3$ are as defined above which comprises the esterification of an acid derivative of the formula

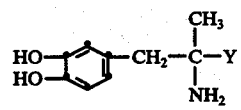

or an acid addition salt thereof with a compound of the formula

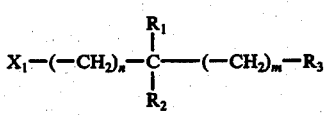

wherein Y is —COOH, —COhalogen or —carboxylic acid salt and $n$, $m$, $R_1$, $R_2$ and $R_3$ are as defined above and X is hydroxyl, alkali metal —O—, halogen or a substituted —SO$_3$— group. The esterification is carried out under conventional reaction conditions.

In a preferred embodiment of the present invention, the process is carried out with the amino acid portion of the molecule being in the L stereo configuration.

The expressions "(—CH$_2$)$_n$" and "(—CH$_2$)$_m$" also include the branched chain alkylene radicals such as

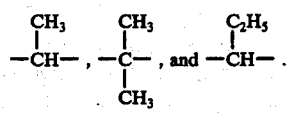

Preferably $n$ and $m$ are 0 or 1.

The terminology "a monocyclic or bicyclic . . . . 5 to 6 members" means that the compounds contains one or two ring nitrogen atoms with an optional ring sulfur atom and from 3 to 12 ring carbon atoms. The compounds further contain one or two rings with 5 or 6 members in each ring and the rings may be substituted by such groups as halogen, hydroxyl, amino or other such groups.

The terminology "$R_4$ contains up to 21 carbon atoms .... 1 hetero atom" signifies that $R_4$ contains a total of from 1 to 21 carbon atoms and is either a hydrocarbon radical or an acyl radical of the formula

wherein R is an acylic or a monocyclic radical with not more than 1 hereto atom. As is hereinafter pointed out in the example, the R group may be an alkyl group, a heterocyclic radical or any other such radical. The nature of this R group does not appear to be critical and it may be widely varied.

The expression "pharmaceutically acceptable acid addition salt" is an expression well known in the art and includes those compounds which are made by the reaction of the free base with an inorganic or organic acid. It includes the hydrochloride, the hydrobromide, salts with sulfuric acid and the like.

The phrase "the L isomer of an amino acid, substantially free of the D isomer" means that the D isomer is present in amounts not exceeding about 10%. However, it is desirable that the D isomer be substantially absent from the composition. In the examples which follow, when the L isomer is designated, the compound is substantially 100% (i.e. well over 99%) in the L configuration.

The terminology "blocking groups" signifies any group which will protect the amino or hydroxyl groups during the reaction. Among the suitable blocking groups for the nitrogen atom are carbobenzyloxy, paramethoxy-carbobenzyloxy, trifluoroacetyl, HCl and the like. Suitable blocking groups for the hydroxyl groups are diphenyl ketal for both hydroxyl groups and the acetyl and carbobenzyloxy for the individual hydroxyl groups as well as other such radicals. The substituents in the "substituted —$SO_3$—group" can be substantially any radical since these groups are readily cleaved during the esterification reaction and the nature of the group is not at all critical.

The term "reducible groups" signifies any group which can be replaced by the hydrogen atom or can be partially or completely saturated by hydrogen. Such groups include —CH=CH—, —C|C—, halogen, —$NO_2$, —CN and the like.

The expression "acylating agent" designates an activated carboxylic acid derivative such as a carboxylic acid anhydride (including mixed anhydrides) or a compound of the formula

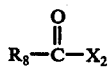

wherein $R_8$ is an organic radical and $X_2$ is an easily removable group such as halogen, p-nitrophenoxy, phenoxy or the like.

When racemic mixtures are formed in accordance with the synthesis of the present invention, it is sometimes desirable to separate the mixtures into their L and D isomers. The isomers can be separated at any point in the synthesis and in most instances it is desired to separate them prior to forming the final product. In other instances (as when $R_1$ and $R_2$ are different groups and the acid portion is in the L configuration), a mixture of diastereomers is formed as the final product and these may be directly separated by crystallization or the formation of simple derivatives with crystallization. It is by far preferable, however, to start with the desired isomer (i.e. the L isomer) when the single isomer is desired. It is also possible to form a diastereomer of the racemic mixtures formed in accordance with the present invention to effect separation. In such instances, an optically active acid such as tartaricoacid, 10-camphor sulfonic acid, malic acid, pyroglutamic acid, methoxy acetic acid and the like may be used. The selection of the particular acid may be made as desired and would be obvious to one skilled in the art.

The compounds of the present invention can be used in the form of compositions preferably administered in unit dosage form such as tablets, pills, capsules, powders, granules, sterile parenteral solutions or suspensions, oral solutions or suspensions and the like. For preparing solid compositions such as tablets, the principal active ingredient is mixed with conventional tableting ingredients such as corn starch, lactose, sucrose, sorbitol, talc, stearic acid, magnesium stearate, dicalcium phosphate, gums and fractionally similar materials as pharmaceutical diluents or carriers. The tablets or pills of the novel compositions can be laminated or otherwise compounded to provide a dosage from affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The compounds are also useful when administered in the form of suppositories or with a penetrant such as dimethyl sulfoxide.

The liquid forms in which the novel composition of the present invention may be incorporated for administration include suitably flavored emulsions with edible oils, such as, cottonseed oil, sesame oil, coconut oil, peanut and the like, as well as elixirs and similar pharmaceutical vehicles. Suitable dispersing or suspending agents for aqueous suspensions include synthetic and natural gums, such as, tragacanth, acacia, alginate, dextran, sodium carboxymethylcellulose, methylcellulose, polyvinylpyrrolidone, gelatin and the like. Sterile suspensions or solutions are required for parenteral use. Isotonic preparations containing suitable preservatives are also highly desirable for injection use.

The term single dosage form as used in the specification refers to physically discrete units suitable as unitary dosage for warm-blooded animal subjects, each unit containing a predetermined quantity of active material calculated to produce the desired therapeutic effect in association with the required pharmaceutical diluent, carrier or vehicle. The specifications for the novel single dosage forms of this invention are dictated by and are directly dependent on (a) the unique characteristics of the active material and the particular therapeutic effect to be achieved, and (b) the limitations inherent in the art of compounding such an active material for therapeutic use in warm-blooded animals as disclosed in detail in this specification. Examples of suitable oral single dosage forms in accord with this invention are tablets, capsules, pills, powder packets, granules, wafers, cachets, teaspoonfuls, dropperfuls, ampules, vials, segregated multiples of any of the foregoing, and other forms as herein described.

The following examples are given to illustrate the invention and are not intended to limit it in any manner. All parts are given in parts by weight unless otherwise expressed. The "reduced pressure" employed in the following examples is 15 to 25 mm. Hg at 25° to 35° C. (unless otherwise indicated). When reduced pressure is employed to remove a solvent, the resultant product is oftentimes a solvate and thus the example refers to the formation of a "concentrated" product although all of the solvent has been removed with the exception of that bound in the product.

EXAMPLE 1

A. Preparation of L-3-(3,4-diphenylmethylenedioxy-phenyl)-2-methylalanine hydrochloride A mixture of 19.3 g. (0.0777 mole) of L-3-(3,4-dihydroxyphenyl)-2-methylalanine hydrochloride [L-α-methyldopa hydrochloride] and 37 g. (0.156 mole) of dichlorodiphenylmethane is immersed with slow stirring in a preheated oil bath at 190° C. After reaction has started, as evidenced by vigorous gas evolution, the reaction mixture is stirred rapidly for six minutes at 190° C. removed from the hot oil bath and allowed to cool to 25° – 30° C. The crude product from 12 runs is combined, slurried with 3 l. of diethyl ether filtered, washed with an additional 2 l. of diethyl ether and dried at 30° C. under 50 mm. pressure. Recrystallization is accomplished by dissolving the product in ethanol and adding ethyl acetate to precipitate the product. The procedure gives 255 g. (66.4%) of L-3-(3,4-diphenylmethylenedioxyphenyl)-2-methylalanine hydrochloride, m.p. 267° – 268° C. dec. Anal. calcd. for $C_{23}H_{21}NO_4HCl$: C, 67.07; H, 5.39; N, 3.40; Found: C, 66.91; H, 5.29; N, 3.34.

B. Preparation of L-N-carbobenzyloxy-3-(3,4-diphenylmethylenedioxyphenyl)-2-methylalanine A mixture of 175 g. (0.425 mole) of L-3-(3,4-diphenylmethylenedioxyphenyl)-2-methylalanine hydrochloride, 1750 ml. of acetone and 1750 ml. of water is stirred under nitrogen at a temperature below 10° C. while the pH is adjusted to 12.0 by the slow addition of a 10% sodium hydroxide solution. Carbobenzyloxy chloride, 93 g. (0.545 mole) is added dropwise over 5 – 7 minutes to the reaction mixture at 20° – 30° C. accompanied by the simultaneous addition of a 10% sodium hydroxide solution to maintain a pH of 12.0 – 12.2. After addition of the carbobenzyloxy chloride is complete, the reaction mixture is stirred at 25° – 30° C. for three hours. Most of the acetone is then removed under reduced pressure at 25° to 35° C. to precipitate the sodium salt of the desired N-carbobenzyloxy derivative. The sodium salt is extracted into 1.5 l. of ethyl acetate, washed with 200 ml. of 5% sodium hydroxide solution and 200 ml. of a saturated sodium chloride solution and then dried over magnesium sulfate. After adding 17.5 g. of decolorizing carbon and filtering through a magnesium sulfate pad, solvents are removed under reduced pressure at 25° to 35° C. The residue is slurried two times with 1 l. of a 20% ethyl ether-80% hexane (by volume) solution and filtered to give the sodium salt of the desired N-carbobenzyloxy derivative. This sodium salt is dissolved in 1.5 l. of ethyl acetate, cooled to 10° C. and acidified to pH 2 with 6 N hydrochloric acid. The ethyl acetate extract is washed with 200 ml. of a saturated sodium chloride solution, dried over magnesium sulfate, filtered and concentrated under reduced pressure at 25° to 35° C. The N-carbobenzyloxy derivative is dried further at 25° – 30° C. and 0.2 – 0.3 mm. Hg to give 169 g. (78.0%) of L-N-carbobenzyloxy-3-(3,4-diphenylmethylenedioxyphenyl)-2-methylalanine.

C. Preparation of succinimidomethyl L-N-carbobenzyloxy-3-(3,4-diphenylmethylenedioxyphenyl)-2-methylalaninate A solution of 13.5 g. (0.0265 mole) of L-N-carbobenzyloxy-3-(3,4-diphenylmethylenedioxyphenyl)-2-methylalanine, 2.7 g. (0.027 mole) of triethylamine and 5.19 g. (0.029 mole) of N-bromomethylsuccinimide in 35 ml. of dry dimethylformamide is stirred at 25° – 30° C. for 16 hours. The reaction mixture is poured into 400 ml. of ice water and the product extracted into 200 ml. of a 50% chloroform-50% diethyl ether (by volume) mixture. The organic extract is washed with 50 ml. of a dilute (5%) sodium carbonate solution and 50 ml. of a saturated sodium chloride solution and then dried over anhydrous magnesium sulfate to remove water. After filtering and concentrating under reduced pressure, the residue is recrystallized. Recrystallization is accomplished by dissolving the product in ethanol and adding hexane to precipitate the product. The process gives 12.1 g. (73.6%) of succinimidomethyl L-N-carbobenzyloxy-3-(3,4-diphenylmethylenedioxy)phenyl)-2-methylalaninate, m.p. 143.0° – 145.0° C.

Anal. calcd. for $C_{36}H_{32}N_2O_8$: C, 69.66; H, 5.20; N, 4.51; Found: C, 69.83; H, 5.14; N, 4.52.

Preparation of succinimidomethyl L-3-(3,4-dihydroxyphenyl)-2-methylalaninate hydrochloride hydrate A suspension of 6.6 g. (0.0106 mole) of succinimidomethyl L-N-carbobenzyloxy-3-(3,4-diphenylmethylenedioxyphenyl)-2-methylalaninate in 180 ml. of absolute ethanol and 9 ml. of a 9.6 N. ethanolic-anhydrous hydrogen chloride solution is hydrogenated with 3.3 g. of a 10% palladium-on-carbon catalyst at an initial pressure of 30 p.s.i. until hydrogen uptake is complete. After removal of catalyst by filtration, the filtrate is concentrated under reduced pressure. The residue is extracted with 50 ml. of benzene and then 50 ml. of ethyl acetate. The insoluble solid is then shaken with 50 ml. of a 10% ethanol-90% ethyl acetate (by volume) mixture and 10 ml. of a saturated sodium carbonate solution. After filtration, the filtrate is dried over anhydrous magnesium sulfate, filtered and concentrated under reduced pressure. The residue is redissolved in 25 ml. of absolute ethanol, treated with 5 ml. of a 9.6 N ethanolic-anhydrous hydrogen chloride solution and concentrated under reduced pressure to give 2.5 g. (62.7%) of succinimidomethyl L-3-(3,4-dihydroxyphenyl)-2-methylalaninate hydrochloride hydrate, homogeneous upon thin layer chromatography [fluorescent silica gel plate, 30% methanol-70% benzene (by volume) solvent] with an observed Rf = 0.5.

Anal. calcd. for $C_{15}H_{18}N_2O_6.HCl.H_2O$: C, 47.81; H, 5.62; N, 7.44 Found: C, 48.09; H, 5.74; N, 7.42

EXAMPLE 2

A. Preparation of N-(1-chloroethyl)-succinimide

N-vinylsuccinimide, 50.0 g. (0.40 mole) is dissolved in 1000 ml. carbon tetrachloride, 5.20 g. (0.020 mole) of stannic chloride is added and the mixture is stirred while saturating with hydrogen chloride for 6 hours at 20° – 30° C. After 24 hours, the mixture is resaturated with hydrogen chloride for 1.5 hours. At the end of 48 hours, the solution is decanted and the gummy residue is washed with ten 100 ml. portions of carbon tetrachloride. The combined extracts are slurried with 10 g. of diatomaceous earth, filtered and the filtrate concentrated under reduced pressure to approximately 400 ml. The N-(1-chloroethyl)-succinimide is filtered and dried at 20° – 30° C. under reduced pressure to yield 38.4 g. (59%) of white solid melting at 83.5° – 84.5° C.

B. Preparation of α-succinimidoethyl L-N-carbobenzyloxy-3-(3,4-diphenylmethylenedioxyphenyl)-2-methylalaninate A mixture of 30.66 g. (0.060 mole) L-N-carbobenzyloxy-3-(3,4-diphenylmethylenedioxyphenyl)-2-methylalanine, 9.70 g. (0.060 mole) of N-(1-chloroethyl)-succinimide, 6.07 g. (0.060 mole) of triethylamine and 75 ml. of dry dimethylformamide is stirred at 95° for 19 hours. The reaction mixture is poured into 750 ml. of water and the product extracted into three 500 ml. portions of ethyl acetate. The combined organic extracts are washed with three 300 ml. portions of 5% sodium hydroxide solution, then three times with 300-ml. of a saturated sodium chloride solution and dried over anhydrous magnesium sulfate. After filtering, the solution is treated with 5 g. of charcoal, filtered and the solvent is evaporated under reduced pressure to give 37.90 g. (99%) of α-succinimidoethyl L-N-carbobenzyloxy-3-)3,4-diphenylmethylenedioxyphenyl)-2-methylalaninate as a mixture of diastereomeric isomers (α and β).

C. Preparation of α-succinimidoethyl L-3-(3,4-dihydroxyphenyl)2-methylalaninate hydrochloride A suspension of 20.18 g. (0.032 mole) of α-succinimidoethyl L-N-carbobenzyloxy-3-(3,4-diphenylmethylenedioxyphenyl)-2-methylalaninate in 275 ml. of 25% absolute ethanol-75% ethyl acetate (by volume) solution is hydrogenated with 8.5 g. of 10% palladium-on-carbon catalyst at an initial pressure of 40 p.s.i. and room temperature for 23 hours. The catalyst is filtered and the filtrate evaporated under reduced pressure at 30° to 40° C. The residue is dissolved in 250 ml. of 10% ethanol-90% ethyl acetate (by volume) solution and stirred with 20 ml. of saturated sodium carbonate solution and approximately 30 g. of anhydrous sodium carbonate for 10 minutes. After filtration, the filtrate is dried over anhydrous magnesium sulfate, filtered and evaporated to dryness under reduced pressure. The residue is dissolved in 130 ml. of dry chloroform, the solution is cooled in an ice bath and saturated with hydrogen chloride for 15 minutes. The solid is collected, washed by suspension in 100 ml. of anhydrous ether three times and then slurried in 300 ml. of ethyl acetate under $N_2$ in a stoppered flask at room temperature overnight. The α-succinimidoethyl L-3-(3,4-dihydroxyphenyl)-2-methylalaninate hydrochloride is collected, stirred in 300 ml. of hexane for 2 hours and dried in a vaccum desiccator over $CaCl_2$ to give 8.32 g. (62%) of hydrochloride as a mixture of α and β isomers, observed Rf = 0.7 upon thin layer chromatography [fluorescent silica gel plate, 50% methanol-50% benzene (by volume) solvent].

Anal. calcd. for $C_{16}H_{20}N_2O_6.HCl.1/2\ CH_3CO_2C_2H_5$: C, 51.86; H, 6.05; N, 6.7 Found: C, 51.98; H, 5.87; N, 6.65

EXAMPLE 3

A. Separation of α-succinimidoethyl L-N-carbobenzyloxy-3-(3,4-dihydroxyphenylmethylenedioxyphenyl)-2-methylalaninate isomers The mixture of diasteromeric isomers of Example 2, 150.5 g., is dissolved in a boiling mixture of 1200 ml. of benzene and 100 ml. of absolute methanol, filtered and the filtrate is concentrated to a volume of approximately 700 ml.. Absolute methanol, 100 ml., is added to the solution, which then is diluted to cloudiness with 1000 ml. of hexane, seeded and scratched to induce crystallization. The mixture is cooled at 5° C. for about 16 hours and the crude crystalline α-isomer is then collected, washed by suspension in 200 ml. of a 50:50 mixture (by volume) of benzene and hexane and dried at 70° C. The product weighs 68.1 g. and melts at 185.5° – 191° C. An analytical sample melts at 199.5° – 201.5° C. after two additional recrystallizations.

Anal. calcd. for $C_{37}H_{34}N_2O_8$: C, 70.02; H, 5.40; N, 4.41; Found: C, 70.22; H, 5.52; N, 4.29

The combined mother liquors and washings from the α-isomer are evaporated to dryness under reduced pressure at 60° C. to give 79.3 g. of the β-isomer as a very viscous oil.

B. Preparation of α-succinimidoethyl L-3-(3,4-dihydroxyphenyl)-2-methylalaninate hydrochloride dihydrate (β-isomer)

A solution of 10.0 g. (0.016 mole) of α-succinimidoethyl L-N-carbobenzyloxy-3-(3,4-diphenylmethylenedioxyphenyl)-2-methylalaninate (β-isomer) in 140 ml. of 25% absolute ethanol-75% ethyl acetate (by volume) solution is hydrogenated with 4.2 g. of 10% palladium-on-carbon catalyst at an initial pressure of 40 p.s.i. and room temperature for 20 hours until hydrogen uptake is complete. The catalyst is filtered under nitrogen, the filtrate is acidified with 2.0 ml. of 9.4 N ethanolic hydrogen chloride and evaporated to dryness under reduced pressure at 30 to 40° C. The amorphous solid residue is dissolved in 50 ml. warm 95% ethanol (5% water), filtered and the filtrate is diluted to incipient cloudiness with anhydrous ether (68 ml.), seeded and scratched to induce crystallization. The product is collected and stirred in 300 ml. of anhydrous ether to remove any diphenylmethane. After one hour, the solid is collected and dried at 70° C. overnight to give 3.7 g. of material melting at 123° – 126° C. (dec.). Recrystallization from 20 ml. of 95% ethanol affords 3.36 g. (51%) of α-succinimidoethyl L-3-(3,4-dihydroxyphenyl)-2-methylalaninate hydrochloride dihydrate (β-isomer) as the dihydrate melting at 129° – 131° C. (dec.) (dried at 70° C. overnight), homogeneous upon thin layer chromatography [fluorescent silica gel plate, 50% methanol-50% benzene (by volume) solvent], Rf = 0.7.

Anal. calcd. for $C_{16}H_{20}N_2O_6.HCl.2H_2O$: C, 47.00; H, 6.16; N, 6.85 Found: C, 46.85, 47.09; H, 6.12, 6.16; $[\alpha]_D^{240} = +33.46°(C = 1.5\ CH_3OH)$

EXAMPLES 4

A. Preparation of α-succinimidoethyl L-3-(3,4-dihydroxyphenyl)-2-methylalaninate hydrochloride (60 -isomer)

A solution of 10.0 g. (0.016 mole) of α-succinimidoethyl L-N-carbobenzyloxy-3-(3,4-diphenylmethylenedioxyphenyl)-2-methylalaninate (α-isomer) in 140 ml. of 25% absolute ethanol-75% ethyl acetate (by volume) solution is hydrogenated with 4.2 g. of a 10% palladium-on-carbon catalyst at an initial pressure of 40 p.s.i. and room temperature for 27-½ hours until hydrogen uptake is complete. Two ml. of a 9.4 N ethanolic solution of anhydrous hydrogen chloride is added and catalyst removed by filtration through a pad of diatomaceous earth. After concentrating under reduced pressure, the residue is extracted by shaking with 200 ml. diethyl ether, twice with 200 ml. benzene and finally twice with 200 ml. of diethyl ether. The material remaining after these extractions is the desired α-succinimidoethyl L-3-(3,4-dihydroxyphenyl)-2-methylalaninate hydrochloride (α-isomer) diethyl ether solvate, Rf = 0.7 [thin layer chromatography fluorescent silica gel plate, 50% methanol-50% benzene (by volume) solvent] contaminated with 12% diphenylmethane. $[\alpha]_D^{24} = -18.75$ (C, 1.68, $CH_3OH$).

EXAMPLE 5

A. Preparation of 2-trifluoroacetamidoethyl L-N-cabobenzyloxy-3-(3,4-diphenylmethylenedioxyphenyl)-2-methylalaninate A solution of 5.09 g. (0.010 mole) of L-N-carbobenzyloxy-3-(3,4-diphenylmethylenedioxyphenyl)-2-methylalanine, 1.01g. (0.010 mole) of triethylamine and 1.76 g. (0.010 mole) of N-(2-chloroethyl-2,2,2-trifluoroacetamide in 20 ml. dry dimethylformamide is stirred at 110° C. for 20 hours under nitrogen. The cooled reaction mixture is poured into 500 ml. of ice water and the product extracted into three 500 ml. portions of ethyl acetate. The combined extracts are washed with 200 ml. of water, dried ($MgSO_4$), filtered and concentrated to an oil under reduced pressure. The residual oil is redissolved in 100 ml. ethyl acetate, extracted with two 50 ml. portions of a 5% sodium hydroxide solution, washed with 50 ml. of water and dried over magnesium sulfate. Filtering and concentrating under reduced pressure gives 4.92 g. of an oil. Chromatography of this oil on 200 g. of silica gel and elution with a 5% solution of methanol in chloroform affords 4.11 g. (63.4%) of the 2-trifluoroacetamidoethyl L-N-carbobenzyloxy-3-(3,4-diphenylmethylenedioxyphenyl)-2-methylalaninate as an oil, homogeneous upon thin layer chromatography [fluorescent silica gel plate developed with 5% methanol-95% chloroform (by volume)] Rf = 0.8.

B. Preparation of 2-trifluoroacetamidoethyl L-3-(3,4-dihydroxyphenyl)-2-methylalaninate hydrochloride A solution of 2.0 g. (0.0031 mole) of 2-trifluoroacetamidoethyl L-N-carbobenzyloxy-3-(3,4-diphenylmethylene-dioxyphenyl)-2-methylalaninate in 125 ml. absolute ethanol and 1.0 g. of a 10% palladium-on-carbon catalyst is hydrogenated at room temperature and an initial pressure of 36 p.s.i. for 5¾ hours until hydrogen uptake is complete. Catalyst is removed by filtration under nitrogen through a diatomaceous earth filter pad and the filtrate is concentrated under reduced pressure at a temperature of 20 to 30° C. The residue is redissolved in 25 ml. absolute ethanol, converted to the hydrochloride by addition of 2 ml. of 7.6 N ethanolic-anhydrous hydrogen chloride solution and then concentrated under reduced pressure. The residue is precipitated twice by dissolving in ethanol and adding sufficient ethyl ether to precipitate the product to give 800 mg. (66.6%) of 2-trifluoroacetamidoethyl L-3-(3,4-dihydroxyphenyl)-2-methylalaninate hydrochloride as the ethanol solvate, homogeneous upon thin layer chromatography [fluorescent silica gel plate developed with 50 % methanol-50% chloroform (by volume)] RF = 0.8.

Anal. calcd. for $C_{14}H_{17}F_3N_2O_5 \cdot HCl \cdot C_2H_5OH$: C, 44.40; H, 5.59; N, 6.47 Found C, 44.55; H, 5.29; N 6.72

EXAMPLE 6

A. Preparation of 2-nicotinamidoethyl L-N-carbobenzyloxy-3-(3,4-diphenylmethylenedioxyphenyl)-2-methylalaninate A solution of 5.84 g. (0.015 mole ) of L-N-carbobenzyloxy-3-(3,4-diphenylmethylenedioxyphenyl)-2-methylalanine, 1.52 g. (0.015 mole) of triethylamine and 2.77 g. (0.015 mole) of N-(2-chloroethyl)-nicotinamide in 20 ml. dry dimethylformamide is stirred under nitrogen at 95° C. for 20 hours. The cooled reaction mixture is poured into 200 ml. of ice water and the product exracted into three 175 ml. portions of ethyl acetate. The combined extracts are washed with 100 ml. of saturated sodium bicarbonate solution, 100 ml. of water and dried ($MgSO_4$). After filtering, solvents are removed under reduced pressure to give 6.28 g. (85%) of 2-nicotinamidoethyl L-N-carbobenzyloxy-3-(3,4-diphenylmethylenedioxyphenyl)-2-methylalaninate, homogeneous upon thin layer chromatography [fluorescent silica gel plate developed with a 20% methanol 80% benzene (by volume) solution] observed Rf = 0.45.

B. Preparation of 2-nicotinamidoethyl L-3-(3,4-dihydroxyphenyl)-2-methylananinate dihydrobromide A mixture of 1.0 g. (2.0 mmole) of 2-nicotinamidoethyl L-N-carbobenzyloxy-3-(3,4-diphenylmethylenedioxyphenyl)-2-methylalaninate and 10 ml. of a 30 – 32% solution of anhydrous hydrogen bromide in acetic acid is allowed to stand at 20° – 25° C. for 30 minutes until gas evolution is complete. The homogeneous solution is concentrated under reduced pressure at 20° – 25° C. and the residue is stirred with 50 ml. diethyl ether for 3 days. The nearly white solid is collected, washed with 50 ml. of anhydrous ethyl ether and dried under high vaccum (0.1 to 0.3 mm. Hg.) at 20° – 25° C. to give 800 mg. (77%) of the 2-nicotinamidoethyl L-3-(3,4-dihydroxyphenyl)-2-methylalaninate dihydrobromide, observed Rf = 0.5 upon thin layer chromatography [fluorescent silica gel plate developed with a solution consisting of equal parts (by volume) of n-butanol, acetic acid, 1% aqueous sodium bisulfite, benzene and acetone].

Anal. calcd. for $C_{18}H_{21}N_3O_5 \cdot 2HBr \cdot 2H_2O$: C, 38.79; H, 4.88; N, 7.54 Found: C, 38.79; H, 4.56; N, 7.37

EXAMPLE 7

Preparation of α-chloroethylpivalate

Zinc chloride, 400 mg., is fused at 0.2 - 0.5 mm pressure and cooled to 25° - 30° C. under nitrogen. Pivaloyl chloride, 48 g. (0.40 mole) is added to the fused zinc chloride followed by acetaldehyde, 19.2 g. (0.44 mole). During addition of the acetaldehyde, which is done as rapidly as possible, the reaction mixture is stirred and cooled to prevent loss of acetaldehyde due to the exothermic nature of the reaction. After heating at reflux for 1 hour, distillation gives 36 g. (55%) of α-chloroethylpivalate, b.p. 32° - 4° C. at 4 mm.

B. Preparation of α-pivaloyloxyethyl L-N-carbobenzyloxy3-(3,4-diphenylmethylenedioxyphenyl)-2-methylalaninate To a stirred solution of 9.0 g. (0.018 mole) of L-N-carbobenzyloxy-3-(3,4-diphenylmethylenedioxyphenyl)2-methylalanine in 25 ml. dry dimethylformamide is added 1.80 g. (0.018 mole) of triethylamine followed by 2.96 g. (0.018 mole) of α-chloroethylpivalate. After stirring at 90° - 95° C. for 20 hours, the reaction mixture is poured into 350 ml. water and the product extracted three times with 100 ml. of ethyl ether. The ether extracts are combined, washed with 50 ml. of a 5% sodium hydroxide solution, 50 ml. of water and dried over anhydrous magnesium sulfate. After filtering, solvents are removed under reduced pressure to give 7.9 g. (68.9%) of crude α-pivaloyloxyethyl L-N-carbobenzyloxy-3-(3,4-diphenylmethylenedioxyphenyl)-2-methylalaninate.

C. PREPARATION OF α-pivaloyloxyethyl L-3-(3,4-dihydroxyphenyl)-2-methylalaninate hydrochloride A solution of 7.8 g. of α-pivaloyloxyethyl L-N-carbobenzyloxy-3-(3,4-diphenylmethylenedioxyphenyl)-2-methylalaninate in 140 ml. absolute ethanol and 11 ml. of an 8 N ethanolic-anhydrous hydrogen chloride solution is hydrogenated with 3.7 g. of a 10% palladium-on-carbon catalyst at 20° - 25° C. and an initial pressure of 35 p.s.i. for 19 hours until hydrogen uptake ceases. After removing catalyst of filtration, ethanol is removed under reduced pressure. The residue is stirred overnight with 80 ml. benzene. The benzene is removed by decantation, replaced with 80 ml. of hexane stirred and the hexane decanted off. The residue is dissolved in 300 ml. ethyl acetate, stirred briefly with a mixture of 5 g. of solid sodium carbonate and 5 ml. saturated sodium carbonate solution and dried over anhydrous magnesium sulfate. After filtering, 3 ml. of 9.6 N ethanolic-anhydrous hydrogen chloride is added and the solution concentration under reduced pressure to dryness. Further drying at 65° C. and 0.2 mm. pressure gives 2.16 g. (47.2%) of the α-pivaloyloxyethyl ester hydrochloride.

Anal. calcd. for $C_{17}H_{25}NO_6 \cdot HCl$: C, 54.32; H, 6.97; N, 3.73 Found: C, 54.47; H, 7.36; N, 3.39

EXAMPLE 8

A. Preparation of L-N-carbobenzyloxy-3-(3,4-dihydroxyphenyl)-2-methylalanine To a stirred solution of 3.0 g. (0.0126 mole) of L-3-(3,4-dihydroxyphenyl)-2-methylalanine sesquihydrate in 20 ml. of 2 N sodium hydroxide solution maintained at 0° C. under a nitrogen atmosphere is added a solution of 3 ml. of carbobenzyloxy chloride in 10 ml. of diethyl ether. After stirring at 0° C. for one hour, followed by one hour at 25° C., the reaction mixture is extracted with 50 ml. of diethyl ether. The aqueous portion is acidified to pH 3 - 4 with a 6 N hydrochloric acid solution and the crude product is extracted into 100 ml. of ethyl acetate and washed three times with 25 ml. of water. After drying over anhydrous magnesium sulfate and filtering, solvent is removed under reduced pressure to give 1.5 g. (34.5%) of L-N-carbobenzyloxy-3-(3,4-dihydroxyphenyl)-2-methylalanine as a viscous oil.

B. Preparation of pivaloyloxymethyl L-3-(3,4-dihydroxyphenyl)-2-methylalaninate hydrochloride A mixture of 2.1 g. (6.1 mmole) of L-N-carbenzyloxy-3-(3,4-dihydroxyphenyl)-2-methylalanine, 0.93 g. (6.2 mmole) of chloromethylpivalate, 0.63 g. (6.3 mmole) of potassium bicarbonate and 0.15 g. potassium iodide in 60 ml. of acetone and 4 ml. of water is stirred at reflux under nitrogen for 18 hours. After concentrating under reduced pressure, 50 ml. of water is added and the N-carbobenzyloxy derivative of the desired ester is extracted with three 50 ml. portions of diethyl ether. The ether extract is washed with 50 ml. of water, dried over anhydrous magnesium sulfate and concentrated under reduced pressure. The oily residue is dissolved in 100 ml. of absolute ethanol and 4 ml. of a 9.6 N ethanolic-anhydrous hydrogen chloride solution and hydrogenated with 1 g. of a 10% palladium-on-carbon catalyst at an initial pressure of 39 p.s.i. for 24 hours. After removing catalyst by filtration, the filtrate is concentrated under reduced pressure. The residue is dissolved in 5 ml. of water, made basic to pH 8 with a saturated sodium carbonate solution and the insoluble product extracted into 25 ml. of ethyl acetate. After drying over anhydrous magnesium sulfate and filtering, 1 ml. of 9.6 N ethanolic-anhydrous hydrogen chloride solution is added and the solution is concentrated under reduced pressure to give 0.50 g. (22.6%) of the hydrochloride of pivaloyloxymethyl L-3-(3,4-dihydroxyphenyl)-2-methylalaninate hydrochloride, Rf = 0.86 upon thin layer chromatography [fluorescent silica gel plate developed with a 5:2:3 (by volume) mixture of n-butanol:acetic acid:water].

Anal. calcd. for $C_{16}H_{23}NO_6 \cdot HCl$: C, 53.11; H, 6.69; N, 3.87 Found: C, 53.76; H, 6.64; N, 3.69

EXAMPLE 9

A. Preparation of 1,2-ethylene bis L-N-carbobenzyloxy-3-(3,4-dihydroxyphenyl)-2-methylalaninate A solution of 7.8 g. (0.023 mole) of L-N-carbobenzyloxy-3-(3,4-dihydroxyphenyl)-2-methylalanine, 1.88 g. (0.01 mole) of 1,2-dibromoethane and 2.1 g. (0.021 mole) of triethylamine in 20 ml. dimethylformamide is heated at 85° - 90° C. for 10 hours and then poured into 200 ml. water. The blocked bis ester is extracted with three 100 ml. portions of ethyl acetate and washed with 100 ml. of a saturated sodium bicarbonate solution and 100 ml. of a saturated sodium chloride solution. After drying over anhydrous magnesium sulfate and concentrating under reduced pressure at 30° - 40° C., 5.3 g. (74%) of 1,2-ethylene bis L-N-carbobenzyloxy-3-(3,4-dihydroxyphenyl)-2-methylalaninate is obtained.

B. Preparation of 1,2-ethylene bis L-3-(3,4-dihydroxyphenyl)-2-methylalaninate dihydrochloride A solution of 5.0 g. (6.98 mmole) of 1,2-ethylene bis L-N-carbobenzyloxy-3-(3,4-dihydroxyphenyl)-2-methylalaninate in 120 ml. of a 25% methanol-75% ethyl acetate (by volume) mixture is hydrogenated at an initial pressure of 35 p.s.i. with 2 g. of 10% palladium-on-carbon catalyst until hydrogen uptake is complete. After filtering to remove catalyst, solvents are removed under reduced pressure. The residue is dissolved in a 10% ethanol - 90% ethyl acetate (by volume) mixture, stirred with 5 ml. of a saturated sodium carbonate solution and 5 g. of solid sodium carbonate. Anhydrous magnesium sulfate is added, the mixture is filtered and the filtrate acidified with 1 ml. of 9.6 N ethanolic-anhydrous hydrogen chloride solution. Solvents are removed under reduced pressure at a temperature of 20 to 30° C. to give 1,2-ethylene bis L-3-(3,4-dihydroxyphenyl)-2-methylalaninate dihydrochloride as the ethyl acetate solvate.

Anal. calcd. for $C_{22}H_{28}N_2O_8 \cdot 2HCl \cdot 2C_4H_8O_2$: C, 51.65; H, 6.65; N, 4.07 Found: C, 50.91; H, 6.69; N, 4.27

EXAMPLE 10

A. Preparation of 1,3-propylene bis L-N-carbobenzyloxy3-(3,4-dihydroxyphenyl)-2-methylalaninate A solution of 7.8 g. (0.023 mole) of L-N-carbobenzyloxy-3-(3,4-dihydroxyphenyl)-2-methylalaninate, 2.1 g. (0.020 mole) of triethylamine and 2.02 g. (0.010 mole) of 1,3-dibromopropane in 20 ml. dimethylformamide is heated under nitrogen for 15 hours at 95° C. and then poured into 200 ml. of water. The product is extracted with three 100 ml. portions of ethyl acetate and washed with 50 ml. of a dilute sodium bicarbonate solution (5%), 50 ml. of water and finally 50 ml. of a saturated solution of sodium chloride. After drying over anhydrous magnesium sulfate and concentrating under reduced pressure, 5.4 g. (73.8%) of 1,3-propylene bis L-N-carbobenzyloxy-3-(3,4-dihydroxyphenyl)-2-methylalaninate is obtained.

B. Preparation of 1,3-propylene bis L-3-(3,4-dihydroxyphenyl)-2-methylalaninate dihydrochloride A solution of 5.4 g. (7.39 mmole) of 1,3-propylene bis L-N-carbobenzyloxy-3-(3,4-dihydroxyphenyl)2-methylalaninate in 100 ml. 25% ethanol-75% ethyl acetate (by volume) is hydrogenated at an initial pressure of 35 p.s.i. with 2.5 g. of a 10% palladium-on-carbon catalyst at 25° C. until hydrogen uptake ceases. After removing catalyst by filtration, solvents are removed under reduced pressure. The residue is dissolved in 10% methanol-90% ethyl acetate (by volume), stirred with 5 ml. of a saturated sodium carbonate solution and 5 g. of solid sodium carbonate. Five grams of anhydrous magnesium sulfate is added, the mixture is filtered and the filtrate acidified with 1 ml. of 9.6 N ethanolic-anhydrous hydrogen chloride solution. The solution is concentrated under reduced pressure to about 50 - 60 ml. volume and decanted from an insoluble gum. The gum is stirred with 25 ml. of ethyl acetate, filtered and dried to give 1.74 g. (33%) of 1,3-propylene bis L-3-(3,4-dihydroxyphenyl)-2-methylalaninate dihydrochloride as the ethyl acetate solvate, Rf = 0.56, thin layer chromatography [fluorescent silica gel plate developed with a solution containing equal parts (by volume) of n-butanol, acetone, acetic acid, water and benzene].

EXAMPLE 11

A. Preparation of 1-chloro-1-succinimidopropane

Anhydrous hydrogen chloride is bubbled through a mixture of 10 g. (0.072 mole) of N-propenylsuccinimide and 1.04 g. of stannic chloride for 6 hours. The solution is allowed to stand at room temperature for 10 days, the solution being saturated again with hydrogen chloride gas after 3 days and 4 days. Solvents are removed under reduced pressure at 30° - 40° C. to give 1-chloro-1-succinimidopropane as a yellow oil.

B. PREPARATION OF α-SUCCINIMIDOPROPYL L-N-CARBOBENZYLOXY-3

A solution of 10.2 g. (0.020 mole) of L-N-carbobenzyloxy-3-(3,4-diphenylmethylenedioxyphenyl)-3-methylalanine, 2.1 g. (0.021 mole) of triethylamine and 3.51 g. (0.020 mole) of 1-chloro-1-succinimidopropane in The product is extracted with three 100 ml. portions of ethyl ether and washed with 50 ml. of 5% sodium hydroxide, 50 ml. of water and 50 ml. of a saturated solution of sodium chloride. After drying over anhydrous magnesium sulfate and filtering, solvents are removed under reduced pressure to give 8.6 g. (68%) of α-succinimidopropyl L-N-carbobenzyloxy-3-(3,4-diphenylmethylenedioxyphenyl)-2-methylalaninate, Rf = 0.2, thin layer chromatography [fluorescent silica gel plate developed with chloroform].

C. Preparation of α-succinimidopropyl L-3-(3,4-dihydroxyphenyl)-2-methylalaninate hydrochloride A solution of 8.6 g. (0.014 mole) of α-succinimidopropyl L-N-carbobenzyloxy-3-(3,4-diphenylmethylenedioxyphenyl)-2-methylalaninate in 120 ml. of a 25% ethanol 75% ethyl acetate (by volume) solution is hydrogenated with 4 g. of a 10% palladium-on-carbon catalyst at an initial pressure of 40 p.s.i. for 18 hours until hydrogen uptake ceases. After removing catalyst by filtration, solvents are removed under reduced pressure at 30° - 40° C. The residue is dissolved in 10% ethanol-90% ethyl acetate (by volume) and stirred with 5 ml. of saturated sodium carbonate solution and excess solid sodium carbonate for 2 minutes. Ten grams of anhydrous magnesium sulfate is added, the mixture is filtered and the filtrate acidified with 2 ml. of 9.6 N ethanolic-hydrogen chloride solution. The solution is concentrated to dryness under reduced pressure, 100 ml. ethyl acetate is added and the mixture concentrated again to dryness under reduced pressure. Ethyl acetate, 100 ml., is added and after stirring at 25° C. for 1 hour, the product is removed by filtration and dried under reduced pressure to give 3.0 g. (51.0%) of α-succinimidopropyl L-3-(3,4-dihydroxyphenyl)-2-methyl-alaninate hydrochloride as the ethanol solvate, Rf = 0.63, thin layer chromatography [fluorescent silica gel plate developed with 30% methanol-70% benzene (by volume)].

Anal. calcd. for $C_{17}H_{22}N_2O_6 \cdot HCl \cdot C_2H_5OH$: C, 52.71; H, 6.75; N, 6.47 Found: C, 53.62; H, 6.51; N, 6.32

EXAMPLE 12

A. Preparation of N-chloromethylglutarimide

Thionyl chloride, 8.35 g. (0.070 mole) is added slowly to a solution of 9.0 g. (0.063 mole) of N-hydroxymethylglutarimide in 50 ml. benzene at 40° C. After addition is complete, the solution is stirred at reflux for 1.5 hours and then at room temperature for an additional 1.5 hours. Benzene is removed under reduced pressure at 30° - 40° C. and the residue is distilled to give 5.4 g. (53%) of N-chloromethylglutarimide, b.p. 97° - 100° C. at 0.1 mm.

B. Preparation of glutarimidomethyl L-N-carbobenzyloxy-3-(3,4-diphenylmethylenedioxyphenyl)-2-methylalaninate A solution of 10.2 g. (0.020 mole) of L-N-carbobenzyloxy-3-(3,4-diphenylmethylenedioxyphenyl)-2-methylalanine, 2.02 g. (0.020 mole) of triethylamine and 3.23 g. (0.020 mole) of N-chloromethylglutarimide in 20 ml. dimethylformamide is stirred at 70° C. for 5 hours, then at 20° - 30° C. for 5 hours and finally poured into 200 ml. of water. The product is extracted with three 100 ml. portions of ethyl acetate, washed with 50 ml. of a 5% sodium hydroxide solution, 50 ml. of water and 50 ml. of saturated sodium chloride solution and dried over anhydrous magnesium sulfate. After filtering, solvents are removed under reduced pressure to give 12.1 g. (95%) of glutarimidomethyl L-N-carbobenzyloxy-3-(3,4-diphenylmethylenedioxyphenyl)-2-methylalaninate, $Rf = 0.14$ upon thin layer chromatography [fluorescent silica gel plate developed with chloroform].

C. Preparation of glutarimidomethyl L-3-(3,4-dihydroxyphenyl)-2-methylalaninate hydrochloride A solution of 12 g. (0.0189 mole) of glutarimidomethyl L-N-carbobenzyloxy-3-(3,4-diphenylmethylenedioxyphenyl)-2-methylalaninate in 130 ml. of 25% absolute ethanol-75% ethyl acetate (by volume) is hydrogenated with 5 g. of a 10% palladium-on-carbon catalyst at 20° - 25° C. and an initial pressure of 40 p.s.i. for 18 hours until hydrogen uptake ceases. After removing catalyst by filtration and concentrating to dryness under reduced pressure, the residue is dissolved in 200 ml. of a 10% absolute ethanol-90% ethyl acetate (by volume) solution and stirred with 5 ml. of a saturated sodium carbonate solution and excess solid carbonate for 2 minutes. Ten grams of anhydrous magnesium sulfate is added and after a few minutes is removed by filtration. Solvents are removed under reduced pressure, the residue is washed with 25 ml. of hexane and then 25 ml. of ethyl acetate and dried under reduced pressure. The residue is retreated with sodium carbonate as before to remove the last traces of α-methyl3,4-dihydroxyphenylalanine and converted to the hydrochloride salt with 3 ml. of 9.6 N ethanolic-anhydrous hydrogen chloride to give 3.0 g. (36%) of glutarimidomethyl L-3-(3,4-dihydroxyphenyl)-2-methylalaninate hydrochloride as the ethyl acetate solvate, homogeneous upon thin layer chromatography [fluorescent silica gel plate developed with 30% methanol-70% benzene (by volume)], $Rf = 0.56$.

Anal. calcd. for $C_{16}H_{20}N_2O_6 \cdot HCl \cdot 3/4 C_4H_8O_2$: C, 51.99; H, 6.20; N, 6.38; Found: C, 52.15; H, 6,45; N, 6.53

EXAMPLE 13

A. Preparation of 2-[L-N-carbohenzyloxy-3-(3,4-diphenylmethylenedioxyphenyl)-2-methylalanyloxymethyl]-1,2-benziosothiazol-3(2H)-one-1,1-dioxide A solution of 7.65 g. (0.015 mole) of L-N-carbobenzyloxy-3-(3,4-diphenylmethylenedioxyphenyl)-2-methylalanine, 1.5 g. (0.015 mole) triethylamine and 3.0 g. (0.015 mole) of N-chloromethylsaccharin in 15 ml. dimethylformamide is heated at 75° - 80° C. for 17 hours and then poured into 150 ml. water. The product is extracted with three 100 ml. portions of ethyl acetate, washed with 50 ml. of a saturated sodium bicarbonate solution 50 ml. of water and 50 ml. of a saturated sodium chloride solution and is dried over anhydrous magnesium sulfate. After filtering, solvents are removed under reduced pressure to give 9.3 g. (100%) of 2-[L-N-carbobenzyloxy-3-(3,4-diphenylmethylenedioxyphenyl)-2-methylalanyloxymethyl]-1,2benziosothiazol-3(2H)-one-,1,1-dioxide, $Rf = 0.32$, thin layer chromatography [fluorescent silica gel plate developed with chloroform].

B. Preparation of 2-[L-3-(3,4-dihydroxyphenyl)-2-methyl-alanyloxymethyl]-1,2-benzisothiazol-3(2H)-one-1,1-dioxide hydrochloride A solution of 3.0 g. (0.0043 mole) of the 2-[L-N-carbobenzyloxy-3-(3,4-diphenylmethylenedioxyphenyl)-2-methylalanyloxymethyl]-1,2-benzisothiazol-3(2H)-one1,1-dioxide in 100 ml. absolute ethanol and 5 ml. of 8 N ethanolic -anhydrous hydrogen chloride solution is hydrogenated with 1.5 g. of a 10% palladium-on-carbon catalyst at 20° - 25° C. and an initial pressure of 35 p.s.i. for 20 hours until hydrogen uptake ceases. After removing catalyst by filtration and concentrating to dryness under reduced pressure, the residue is stirred with 50 ml. of ethyl acetate for 1 hour and the ethyl acetate decanted off. The residue is dissolved in 200 ml. of 20% ethanol - 80% ethyl acetate (by volume) and stirred with 10 ml. saturated sodium carbonate solution and excess solid sodium carbonate. Ten grams anhydrous magnesium sulfate is added and after a few minutes is removed by filtration and the filtrate acidified with 1 ml. of 9.6 N ethanolic - anhydrous hydrogen chloride solution. Solvents are removed under reduced pressure to give 0.2 g. (10.0%) of 2-[L -3-(3,4-dihydroxyphenyl)-2-methylalanyloxymethyl]-1,2-benzisothiazol-3(2H) -one-1,1-dioxide hydrochloride as the ethyl acetate solvate, $Rf = 0.74$, thin layer chromatography [fluorescent silica gel plate developed with a solvent consisting of equal parts (by volume) of benzene, water, acetic acid, n-butanol and acetone.

Anal. calcd. for $C_{18}H_{18}N_2O_7S \cdot HC/1/4 \, C_4H_8O_2$: C, 49.08; H, 4.55; N, 6.03 Found: C, 49.27; H, 4.76; N, 5.65

EXAMPLE 14

A. Preparation of 1-methyl-2;[L-N-carbobenzyloxy-3-(3,4-dihydroxyphenyl)-2-methylalanyloxymethyl]-imidazole A solution of 7.8 g. (0.0226 mole) of L-N-carbobenzyloxy-3-(3,4-dihydroxyphenyl)-2-methylalanine, 4.2 g. (0.042 mole) triethylamine and 3.34 g. (0.0256 mole) of 1-methyl-2-chloromethylimidazole in 20 ml. dimethylformamide is heated at 70° - 75° C. for 10 hours and then poured into 200 ml. water. The product is extracted with three 100 ml. portions of ethyl acetate, washed with 50 ml. of a saturated sodium bicarbonate solution, 50 ml. of a saturated sodium chloride solution and concentrated under reduced pressure to give 2.2 g. (22%) of 1-methyl-2-[L-N-carbobenzyloxy-3-(3,4-dihydroxyphenyl)-2-methyl-alanyloxymethyl]-imidazole, homogeneous upon thin layer chromatography [fluorescent silica gel plate developed with 15% methanol-85% chloroform (by volume)] Rf = 0.66.

B. Preparation of L-1-methyl-2-[2-(3,4-dihydroxybenzyl)alanyloxymethyl]-imidazole dihydrochloride dihydrate A solution of 2.1 g. (4.78 mmole) of 1-methyl-2-[L-N-carbobenzyloxy-3-(3,4-dihydroxyphenyl)-2-methylalanyloxymethyl]-imidazole in 100 ml. absolute ethanol is hydrogenated with 1 g. of a 10% palladium-on-carbon catalyst at an initial pressure of 35 p.s.i. for 4 hours. After removing catalyst by filtration and concentrating to 50 ml. under reduced pressure, 2 ml. of 9.6 N ethanolic-anhydrous hydrogen chloride is added and the remainder of solvents are removed under reduced pressure. The residue is stirred with 200 ml. 20% ethanol-80% ethyl acetate (by volume), 10 ml. of saturated sodium carbonate solution and excess solid sodium carbonate. Ten grams of anhydrous magnesium sulfate is added and after a few minutes is removed by filtration. The filtrate is acidified with 1 ml. of 9.6 N ethanolic-anhydrous hydrogen chloride solution. Solvents are removed under reduced pressure to give 0.2 g. (8.5%) of L-1-methyl-2-[2-(3,4-dihydroxybenzyl)-alanyloxymethyl]-imidazole dihydrochloride dihydrate as the ethyl acetate solvate, Rf = 0.3 upon thin layer chromatography [fluorescent silica gel plate developed with a solution consisting of equal parts (by volume) of n-butanol, acetic acid, water, benzene and acetone.

Anal. calcd. for $C_{18}H_{19}N_3O_4.2HCl.2H_2O.1/2C_4H_8O_2$: C, 44.55; H, 6.34; N, 9.17, Found: C, 44.62; H, 6.84; N, 8.95

EXAMPLE 15

A. Preparation of 1-methyl-3-chloromethylhydantoin

Thionyl chloride, 30 ml., is added slowly over 20 minutes to a well stirred mixture of 25 g. (0.173 mole) of 1-methyl-3-hydroxymethylhydantoin and 160 ml. benzene at reflux. After stirring at reflux for 2 hours, the reaction mixture is concentrated to dryness under reduced pressure, 70 ml. of benzene is added and the solution concentrated again to dryness. After repeating this process one more time with 70 ml. benzene, the residue is extracted with three 100 ml. portions of carbon tetrachloride. Removal of solvents under reduced pressure gives 15.7 g. (55.7%) of the 1-methyl-3-chloromethylhydantoin.

B. Preparation of 1-methyl-3-[L-N-carbobenzyloxy-3-(3,4-diphenylmethylenedioxyphenyl)-2-methylalanyloxymethyl]-hydantoin A solution of 10.2 g. (0.020 mole) of L-N-carbobenzyloxy-3-(3,4-diphenylmethylenedioxyphenyl)-2-methylalanine, 2.1 g. (0.021 mole) of triethylamine and 3.25 g. (0.020 mole) of 1-methyl-3-chloromethylhydantoin in 23 ml. dimethylformamide is heated at 70° C. for 18 hours and then poured into 230 ml. water. The product is extracted with three 100 ml. portions of ethyl acetate, washed with 50 ml. of dilute sodium hydroxide solution (5%), 50 ml. of water and 50 ml. of a saturated sodium chloride solution and dried over anhydrous magnesium sulfate. After filtering, solvents are removed under reduced pressure to give 11.7 g. (92%) of 1-methyl-3-[L-N-carbobenzyloxy-3-(3,4-diphenylmethylenedioxyphenyl)-2-methylalanyloxymethyl]-hydantoin.

C. Preparation of L-1-methyl-3-[2-(3,4-dihydroxybenzyl)-alanyloxymethyl]-hydantoin hydrochloride hydrate A solution of 4.0 g. (6.3 mmole) of 1-methyl-3-[L-N-carbobenzyloxy-3-(3,4-diphenylmethylenedioxyphenyl)-2-methylalanyloxymethyl]-hydantoin in 140 ml. absolute ethanol and 2 g. of a 10% palladium-on-carbon catalyst is hydrogenated at an initial pressure of 36 p.s.i. for 20 hours. After removing catalyst by filtration and concentrating to dryness under reduced pressure, the residue is washed with 100 ml. hexane. The hexane insoluble material is dissolved in 150 ml. of 10% methanol-90% ethyl acetate (by volume), stirred with 5 ml. of saturated sodium carbonate solution and excess sodium carbonate and dried over anhydrous magnesium sulfate. After filtering, the filtrate is acidified with 2 ml. of 9.6 N ethanolic-anhydrous hydrogen chloride and concentrated to dryness under reduced pressure. The residue is stirred with 80 ml. ethyl acetate for 3 hours, filtered and dried under reduced pressure to give 0.50 g. (18%) of L-1-methyl-3-[2-(3,4-dihydroxybenzyl)-alanyloxymethyl]-hydantoin hydrochloride hydrate as the ethyl acetate solvate.

Anal. calcd. for $C_{15}H_{19}N_3O_6.HCl.H_2O.1/2C_4H_8O_2$: C, 46.84; H, 6.01; N, 9.64 Found: C, 46.28; H, 6.09; N, 9.06

EXAMPLE 16

A. Preparation of 2-phenoxyethyl L-N-carbobenzyloxy-3-(3,4-diphenylmethylenedioxyphenyl)-2-methylalaninate A solution of 4.5 g. (0.0088 mole) of L-N-carbobenzyloxy-3-(3,4-diphenylmethylenedioxyphenyl)-2-methylalanine, 0.90 g. (0.009 mole) of triethylamine and 1.81 g. (0.009 mole) of 2-bromoethylphenylether in 15 ml. of dimethylformamide is heated at 70° – 75° C. for 24 hours, then cooled and poured in 150 ml. of water. The product is extracted with three 100 ml. portions of ethyl ether, washed with 50 ml. of a 5% sodium hydroxide solution, 50 ml. of water and 50 ml. of a saturated sodium chloride solution and dried over anhydrous magnesium sulfate. After filtering, solvents are removed under reduced pressure to give 4.8 g. (86.5%) of 2-phenoxyethyl L-N-carbobenzyloxy-3-(3,4-diphenylmethylenedioxyphenyl)-2-methylalaninate, homogeneous upon thin layer chromatography [fluorescent silica gel plate developed with chloroform] Rf = 0.91.

B. Preparation of 2-phenoxyethyl L-3-(3,4-dihydroxybenzyl)alaninate hydrochloride hemihydrate A solution of 4.7 g. (7.5 mmole) of 2-phenoxyethyl L-N-carbobenzyloxy-3-(3,4-diphenylmethylenedioxyphenyl)-2-methylalaninate in 120 ml. of absolute ethanol is hydrogenated with 1.7 g. of a 10% palladium-on-carbon catalyst at an initial pressure of 20 p.s.i. for 20 hours. After filtering off catalyst, solvents are removed under reduced pressure and the residue is chromatographed on a column of 75 g. silica gel. Elution with 400 ml. of a 5% methanol-95% benzene (by volume) mixture gives 1.42 g. (58%) of ester base, m.p. 35° – 42° C. homogeneous upon thin layer chromatography [fluorescent silica gel plate developed with 30% methanol-70% benzene (by volume)] Rf = 0.52. The base is converted to the hydrochloride salt by dissolving in 25 ml. of a 50% chloroform-50% methanol (by volume) mixture and acidifying with 2 ml. of 9.6 N ethanolic-anhydrous hydrogen chloride solution. Solvents are removed under reduced pressure to give 2-phenoxyethyl L-3-(3,4-dihydroxybenzyl)-alaninate hydrochloride hemihydrate.

Anal. calcd. for $C_{18}H_{21}NO_5.HCl.1/2H_2O$: C, 57.37; H, 6.15; N, 3.72

Found C, 57.17; H, 6.16; N, 3.41.

EXAMPLE 17

A. Preparation of 2-succinimidoethyl L-N-carbobenzyloxy-3-(3,4-diphenylmethylenedioxyphenyl)-2-methylalaninate A solution of 4.5 g. (8.8 mmole) of L-N-carbobenzyloxy-3-(3,4-diphenylmethylenedioxyphenyl)-2-methyl-alanine, 0.90 g. (9 mmole) of triethylamine and 1.85 g. (9.3 mmole) of N-(2-bromoethyl)-succinimide in 15 ml. of dimethylformamide is heated at 95° C. for 19 hours, then cooled and poured into 150 ml. water. The product is a extracted with three 100 ml. portions of ethyl ether, washed with 50 ml. of a 5% sodium hydroxide solution, 50 ml. of water and 50 ml. of a saturated sodium chloride solution and dried over anhydrous magnesium sulfate. After filtering, solvents are removed under reduced pressure to give 4.8 g. (86%) of 2-succinimidoethyl L-N-carbobenzyloxy-3-(3,4-diphenylmethylenedioxyphenyl)-2-methylalaninate, homogeneous upon thin layer chromatography [fluorescent silica gel plate developed with chloroform] Rf = 0.27.

B. Preparation of 2-succinimidoethyl L-3-(3,4-dihydroxyphenyl)-2-methylalaninate hydrochloride hemihydrate A suspension of 2.5 g. (3.94 mmole) of 2-succinimidoethyl L-N-carbobenzyloxy-3-(3,4-diphenylmethylenedioxyphenyl)-2-methylalaninate in 75 ml. methanol, 75 ml. ethanol and 3 ml. of a 7.6 N ethanolic-anhydrous hydrogen chloride solution is hydrogenated with 1.2 g. of a 10% palladium-on-carbon catalyst at an initial pressure of 20 p.s.i. for 20 hours. After removing catalyst by filtration, solvents are removed under reduced pressure and the residue is stirred with 25 ml. of benzene and then 25 ml. of ethyl acetate. The insoluble material is treated with 100 ml. of 10% ethanol-90% ethyl acetate (by volume), 5 ml. of a saturated sodium carbonate solution and 5 g. solid sodium carbonate. The organic extract is dried over anhydrous magnesium sulfate, then filtered and concentrated under reduced pressure. One ml. of 9.6 N ethanolic-anhydrous hydrogen chloride solution is added. Removal of all solvents under reduced pressure gives 0.5 g. (33%) of the 2-succinimidoethyl L-3-(3,4-dihydroxyphenyl)-2-methylalaninate hydrochloride hemihydrate, homogeneous upon thin layer chromatography [fluorescent silica gel plate developed with 30% methanol-70% benzene (by volume)], Rf = 0.4.

Anal. calcd. for $C_{16}H_{20}N_2O_6.HCl.1/2H_2O$: C, 50,33; H, 5,54; N, 7.34 Found: C, 50.89; H, 5.65; N, 7.22

EXAMPLE 18

A. Preparation of 1,2-ethylene bis [L-N-carbobenzyloxy-3-(3,4-diphenylmethylenedioxyphenyl)-2-methylalaninate]

A solution of 10.18 g. (0.020 mole) of L-N-carbobenzyloxy-3-(3,4-diphenylmethylenedioxyphenyl)-2-methylalanine, 2.12 g. (0.021 mole) triethylamine and 0.99 g. (0.010 mole) of 1,2-dichloroethane in 35 ml. dimethylformamide is stirred under nitrogen at 105° - 110° C. for 28 hours and then poured into 400 ml. ice water. The product is extracted into 800 ml. ethyl ether, washed with 100 ml. of a 5% sodium hydroxide solution, 100 ml. of water, dried over anhydrous magnesium sulfate, filtered and concentrated under reduced pressure. The residue is chromatographed on 800 g. silica gel, 2.25 g. (21.5%) of 1,2-ethylene bis [L-N-carbobenzyloxy-3-(3,4-diphenylmethylenedioxyphenyl)-2-methylalaninate eluted with chloroform.

B. Preparation of L,L-2-[2-(3,4-diphenylmethylenedioxybenzyl)-alanyloxy]-ethyl 2-(3,4-dihydroxybenzyl)alaninate bishydrogen oxalate A solution of 2.25 g. (2.2 mmole) of 1,2-ethylene bis [L-N-carbobenzyloxy-3-(3,4-diphenylmethylenedioxyphenyl)-2-methylalaninate] in 100 ml. absolute ethanol is hydrogenated with 1.2 g. of 10% palladium-on-carbon catalyst at an initial pressure of 30 p.s.i. for 28 hours until hydrogen uptake is complete. After removing catalyst by filtration, solvents are removed under reduced pressure. The residue is stirred with 100 ml. of 10% ethanol-90% ethyl acetate (by volume), 2 ml. of saturated sodium carbonate solution and 3 g. of solid sodium carbonate for 15 minutes and then filtered. The filtrate is dried over anhydrous magnesium sulfate, filtered and concentrated under reduced pressure. The residue is chromatographed over silica gel and eluted with 30% methanol-70% benzene (by volume) to give 220 mg. of product. This product is converted to the oxalate salt with 500 mg. of oxalic acid in 10 ml. of ethanol by precipitation with sufficient ethyl ether. After one more precipitation from 10 ml. of ethanol by adding sufficient ethyl ether, 246 mg. (14%) of L,L-2-[2-(3,4-diphenylmethylenedioxybenzyl)-alanyloxy]-ethyl 2-(3,4-dihydroxybenzyl)-a laninate bishydrogen oxalate is obtained.

Anal. calcd. for $C_{35}H_{36}N_2O_8.2C_2H_2O_4$: C, 59.08; H, 5.08; N, 3.53 Found: C, 59.15; H, 5.18; N, 3.55

EXAMPLE 19

A. Preparation of 2-phthalimidoethyl L-N-carbobenzyloxy-3-(3,4-diphenylmethylenedioxyphenyl)-2-methylalaninate A solution of 10.18 g. (0.020 mole) of L-N-carbobenzyloxy-3-(3,4-diphenylmethylenedioxyphenyl)-2-methylalaninate, 2.12 g. (0.021 mole) triethylamine and 5.08 g. (0.020 mole ) of N-(2-bromoethyl)-phthalimide in 30 ml. dimethylformamide is stirred under nitrogen at 105° - 110° C. overnight and then poured into 600 ml. ice water. The product is extracted into three 100 ml. portions of ethyl ether and washed with 50 ml. of water. The ether extract is dried over anhydrous magnesium sulfate, filtered and concentrated under reduced pressure to give a gummy solid. Chromatography over silica gel and elution with chloroform gives 10.88 g. (80%) of 2-phthalimidoethyl L-N-carbobenzyloxy-3-(3,4-diphenylmethylenedioxyphenyl)-2-methylalaninate, Rf = 0.53, thin layer chromatography [fluorescent silica gel plate developed with chloroform].

B. Preparation of 2-phthalimidoethyl L-3-(3,4-dihydroxyphenyl)-2-methylalaninate hydrochloride A solution of 10.88 g. (0.0159 mole) of 2-phthalimidoethyl L-N-carbobenzyloxy-3-(3,4-diphenylmethylenedioxyphenyl)-2-methylalaninate in 125 ml. ethyl acetate is hydrogenated with 6 g. of a 10% palladium-on-carbon catalyst at an initial pressure of 31 p.s.i. for 5 hours until hydrogen uptake ceases. After removing catalyst by filtration and removing solvents under reduced pressure, the residue is dissolved in 150 ml. absolute ethanol containing 4 ml. of 5.15 N ethanolic-anhydrous hydrogen chloride solution and hydrogenated with 4.3 g. of palladium-on-carbon catalyst at 27 – 38 p.s.i. for 5 days. Additional 4.3 g. amounts of 10% palladium-on-carbon catalyst are added during this time. After removing catalyst by filtration, and concentrating under reduced pressure, the residue is washed with 100 ml. of petroleum ether and dissolved in ethanol. It is precipitated three times from ethanol by adding sufficient ethyl ether to precipitate the product. The product is dried under reduced pressure to give 2.80 g. (41.8%) of 2-phthalimidoethyl L-3-(3,4-dihydroxyphenyl)-2-methylalaninate hydrochloride, m.p. 138.0° – 140° C. dec., homogeneous upon thin layer chromatography [fluorescent silica gel plate developed with 50% methanol-50% benzene (by volume)] Rf = 0.61.

Anal. calcd. for $C_{20}H_{20}N_2O_6 \cdot HCl$: C, 57.07; H, 5.03; N, 6.65; Cl, 8.42 Found: C, 56.31; H, 5.62; N, 6.48; Cl, 8.75

EXAMPLE 20

A. Preparation of 2-acetoxyethyl L-N-carbobenzyloxy-3-(3,4-diphenylmethylenedioxyphenyl)-2-methylalaninate A solution of 10.0 g. (0.0196 mole) of L-N-carbobenzyloxy-3-(3,4-diphenylmethylenedioxyphenyl)-2-methylalanine, 2.39 g. (0.0235 mole) triethylamine and 2.40 g. (0.0196 mole) of 2-chloroethyl acetate in 30 ml. dimethylformamide is stirred under nitrogen at 110° C. for 20 hours and then poured into 500 ml. ice water. The product is extracted into four 200 ml. portions of ethyl ether which are combined and washed with 200 ml. of water, 200 ml. of a 5% sodium hydroxide solution and then 200 ml. of water. After drying over anhydrous magnesium sulfate and filtering, solvents are removed under reduced pressure. The residue is chromatographed on 700 g. silica gel. Elution with 5% methanol-95% chloroform (by volume) gives 5.60 g. (48%) of 2-acetoxyethyl L-N-carbobenzyloxy-3-(3,4-diphenylmethylenedioxyphenyl)-2-methylalaninate.

B. Preparation of 2-acetoxyethyl L-3-(3,4-dihydroxyphenyl)-2-methylalaninate

A solution of 5.60 g. (0.0094 mol) of 2-acetoxyethyl L-N-carbobenzyloxy-3-(3,4-diphenylmethylenedioxyphenyl)-2-methylalaninate in 100 ml. absolute ethanol is hydrogenated with 2.8 g. of a 10% palladium-on-carbon catalyst at an initial pressure of 37 p.s.i. for 24 hours until hydrogen uptake is complete. After removing catalyst by filtration and removing solvents under reduced pressure, the residue is washed with 100 ml. of petroleum ether and dissolved in 124 ml. of 10% ethanol-90% ethyl acetate (by volume). Sodium carbonate, 6.2 g., and 4 ml. of a saturated sodium carbonate solution are added and stirred for 20 minutes. The mixture is filtered, dried over anhydrous magnesium sulfate, filtered again and concentrated under reduced pressure. The residue is chromatographed on silica gel and eluted with 20% methanol-80% benzene (by volume). Recrystallization is accomplished by dissolving it in ethyl acetate and adding sufficient cyclohexane to precipitate it to give 1.01 g. (36%) of 2-acetoxyethyl L-3-(3,4-dihydroxyphenyl)-2-methylalaninate, m.p. 114° – 118° C. dec.

Anal. Calcd. for $C_{14}H_{19}NO_6$: C, 56.55; H, 6.44; N, 4.71 Found: C, 56.64; H, 6.63; N, 4.33

EXAMPLE 21

A. Preparation of 2-benzamidoethyl L-N-carbobenzyloxy-3-(3,4-diphenylmethylenedioxyphenyl)-2-methylalaninate A solution of 10.0 g. (0.0196 mole) of L-N-carbobenzyloxy-3-(3,4-diphenylmethylenedioxyphenyl)-2-methylalanine, 2.11 g. (0.021 mole) triethylamine and 3.64 g. (0.0196 mole) of N-(2-chloroethyl)-benzamide in 20 ml. dimethylformamide is stirred under nitrogen at 110° C. for 20 hours and then poured into 400 ml. ice water. The precipitate is removed by filtration, washed with 100 ml. of water and dissolved in 200 ml. of ethyl ether. The ether solution is washed with 50 ml. of a 5% sodium hydroxide solution, 50 ml. of water and dried over anhydrous magnesium sulfate. Drying agent is filtered off and the filtrate concentrated under reduced pressure to give 11.21 g. (87%) of 2benzamidoethyl L-N-carbobenzyloxy-3-(3,4-diphenylmethylenedioxyphenyl)-2-methylalaninate, Rf = 0.7, thin layer chromatography [fluorescent silica gel plate developed with 5% methanol-95% chloroform (by volume)].

B. Preparation of 2-benzamidoethyl L-3-(3,4-dihydroxyphenyl)-2-methylalaninate oxalate hemihydrate A solution of 11.21 g. (0.017 mole) of 2-benzamidoethyl L-N-carbobenzyloxy-3-(3,4-diphenylmethylenedioxyphenyl)-2-methylalaninate in 100 ml. absolute ethanol is hydrogenated with 5.5 g. of 10% palladium-on-carbon catalyst at an initial pressure of 30 p.s.i. for 7 hours. After removing catalyst by filtration and removing solvents under reduced pressure, the residue is stirred with 100 ml. petroleum ether overnight. The insoluble material is dissolved in 250 ml. of 10% ethanol-90% ethyl acetate (by volume), shaken for 10 minutes with 12 ml. saturated sodium carbonate solution and 12 g. sodium carbonate and filtered. The filtrate is dried over anhydrous magnesium sulfate, filtered and concentrated under reduced pressure. The residue is treated with 1.3 of oxalic acid dissolved in 25 ml. of absolute ethanol, the oxalate salt being precipitated by addition of sufficient ethyl ether. Two more precipitations are carried out by dissolving the product in ethanol and adding sufficient ethyl ether to precipitate the product to give 1.60 g. (23%) of 2-benzamidoethyl L-3-(3,4-dihydroxyphenyl)-2-methylalaninate oxalate hemihydrate, homogeneous upon thin layer chromatography [fluorescent silica gel plate developed with 50% methanol-50% chloroform (by volume)] Rf = 0.44.

Anal. calcd. for $C_{19}H_{22}N_2O_5 \cdot 1/2 H_2C_2O_4 \cdot 1/2H_2O$: C, 58.24; H, 5.86; N, 6.79 Found: C, 58.39; H, 5.73; N, 6.37

EXAMPLE 22

A. Preparation of naphthalimidomethyl L-N-carbobenzyloxy-3-(3,4-diphenylmethylenedioxyphenyl)-2-methylalaninate A solution of 10.2 g. (0.020 mole) of L-N-carbobenzyloxy-3-(3,4-diphenylmethylenedioxyphenyl)-2-methylalanine, 2.02 g. (0.020 mole) of triethylamine and 4.9 g. (0.020 mole) of N-chloromethylnaphthalimide in 50 ml. dimethylformamide is stirred at 90° C. for 20 hours, then poured into 500 ml. ice water. The product is extracted into 200 ml. of ethyl acetate, washed with 50 ml. of a 5% sodium hydroxide solution, 50 ml. of water and 50 ml. of saturated sodium chloride solution and dried over anhydrous magnesium sulfate. After filtering, solvents are removed under reduced pressure to give 13.1 g. (91%) of naphthalimidomethyl L-N-carbobenzyloxy-3-(3,4-diphenylmethylenedioxyphenyl)-2-methylalaninate.

B. Preparation of naphthalimidomethyl L-3-(3,4-dihydroxyphenyl)-2-methylalaninate hydrochloride A solution of 13 g. (0.0181 mole) of naphthalimidomethyl L-N-carbobenzyloxy-3-(3,4-diphenylmethylenedioxyphenyl)-2-methylalaninate in 150 ml. of 25% absolute ethanol-75% ethyl acetate (by volume) is hydrogenated with 5 g. of a 10% palladium-on-carbon catalyst at 25° C. and an initial pressure of 40 p.s.i. for 24 hours until hydrogen uptake is complete. After removing catalyst by filtration and concentrating the filtrate under reduced pressure, the residue is dissolved in 200 ml. of 10% absolute ethanol-90% ethyl acetate (by volume) and stirred with 5 ml. of saturated sodium carbonate solution and 5 g. of solid sodium carbonate for 10 minutes. The mixture is filtered, the filtrated dried with anhydrous magnesium sulfate, filtered again and concentrated under reduced pressure. The residue is washed with 100 ml. of hexane to remove diphenylmethane, dissolved in 25 ml. of absolute ethanol and acidified with 5 ml. of 8 N ethanolic-anhydrous hydrogen chloride solution. Addition of ethyl ether precipitates the hydrochloride salt of the naphthalimidomethyl L-3-(3,4-dihydroxyphenyl)-2-methylalaninate.

EXAMPLE 23

A. Preparation of racemic N-carbobenzyloxy-3-(3,4-dihydroxyphenyl)-2-methylalanine To a stirred solution of 8.0 g. (0.0378 mole) of racemic DL-3-(3,4-dihydroxyphenyl)-2-methylalanine in 60 ml. of 2 N sodium hydroxide solution under nitrogen is added a solution of 9 ml. of carbobenzyloxy chloride in 25 ml. of diethyl ether. After stirring at 0° C. for 1 hour, followed by one hour at 25° C., the reaction mixture is extracted with 50 ml. of diethyl ether. The aqueous portion is acidified to pH 3 with 6 N hydrochloric acid and the crude product is extracted into 100 ml. of ethyl acetate and washed three times with 35 ml. of water. After drying over anhydrous magnesium sulfate and filtering, solvent is removed under reduced pressure to give 4.5 g. (34%) of the racemic N-carbobenzyloxy-3-(3,4-dihydroxyphenyl)-2-methylalanine as a viscous oil.

B. Preparation of racemic pivaloyloxymethyl 3-(3,4-dihydroxyphenyl)-2-methylalaninate hydrochloride A solution of 4.2 g. (0.012 mole) of racemic N-carbobenzyloxy-3-(3,4-dihydroxyphenyl)-2-methylalanine, 1.3 g. (0.013 mole) of triethylamine and 1.26 g. (0.013 mole) of chloromethylpivalate in 20 ml. dimethylformamide is stirred at 90° C. for 20 hours and then poured into 200 ml. water. The product is extracted into 100 ml. of ethyl acetate and washed with 25 ml. of a saturated sodium bicarbonate solution and 25 ml. of water. After drying over anhydrous magnesium sulfate and filtering, the filtrate is concentrated under reduced pressure to give the N-carbobenzyloxy derivative of the desired ester. This material is dissolved in 100 ml. of absolute ethanol containing 10 ml. of a 9.6 N ethanolic-anhydrous hydrogen chloride solution and hydrogenated with 3 g. of a 10% palladium-on-carbon catalyst at an initial pressure of 35 p.s.i. for 24 hours. After removing catalyst by filtration, the filtrate is concentrated under reduced pressure. The residue is dissolved in 25 ml. of water, made basic with a saturated sodium carbonate solution to pH 8 and the insoluble product extracted with 100 ml. of ethyl acetate. After drying over anhydrous magnesium sulfate and filtering, 5 ml. of 9.6 N ethanolic anhydrous hydrogen chloride solution is added and the solution concentrated under reduced pressure to give 1.5 g. (22.6%) of the hydrochloride of the racemic pivaloyloxymethyl 3-(3,4-dihydroxyphenyl)-2-methylalaninate, homogeneous upon thin layer chromatography [fluorescent silica gel plate developed with a 5-2-3 (by volume) mixture of n-butanola-cetic acid-water] Rf = 0.86.

EXAMPLE 24

Preparation of 2-acetamidoethyl L-3-(3,4-dihydroxyphenyl)-2-methylalaninate hydrochloride A slurry of 88.3 g. (0.30 mole) of L-3-(3,4-dihydroxyphenyl)-2-methylalanine hydrochloride ethanol solvate (by concentration of an ethanolic solution of the hydrochloride under reduced pressure) and 146.4 g. (1.42 mole) of N-acetylethanolamine, under nitrogen, is warmed to 104° – 108° C. Thionyl chloride, 84.8 g. (0.713 mole) is added over 15 minutes with stirring. The reaction mixture foams vigorously during the addition. After addition is complete, the reaction mixture is stirred at 104° – 108° C. for 18 hours. Additional thionyl chloride, 42.4 g. (0.357 mole) is added over seven minutes. The reaction mixture is allowed to stir at 104° – 108° C. for another 3½ hours, then cooled to 30° C. and concentrated under reduced pressure to yield a viscous oil. This oil is slurried with 100 ml. of chloroform and the chloroform removed under reduced pressure. This is repeated three more times and then the oil is washed with 100 ml. of benzene which is decanted. The residue is dissolved in 700 ml. of isopropanol and added to 6 l. of ethyl ether. The precipitate which forms is washed with 500 ml. of ethyl ether and shaken with 6 l. of 10% ethanol-90% ethyl acetate (by volume), 150 ml. of saturated sodium carbonate solution and 100 g. of sodium carbonate. The organic extract is dried over anhydrous magnesium sulfate, filtered and concentrated under reduced pressure to give the free base of the acetamidoethyl ester. This base is treated with 15 g. of fumaric acid in 300 ml. of isopropanol and the fumarate salt precipitated by adding sufficient ethyl ether. The fumarate salt is precipitated once more from isopropanol by adding sufficient ethyl ether and then converted back to the free base as before by shaking with 200 ml. of 10% ethanol-90% ethyl acetate (by volume), 20 ml. of saturated sodium carbonate solution and 20 g. solid sodium carbonate. The free base is converted to the hydrochloride salt by dissolving in 100 ml. of absolute ethanol, adding 10 ml. 9.6 N HCl and precipitated by addition to 1 l. of ethyl ether. After three precipitations from ethanol-ethyl ether as carried out above, 15.1 g. (15%) of the hydrochloride salt of the 2acetamidoethyl L-3-(3,4-dihydroxyphenyl)-2-methylalaninate hydrochloride is obtained, Rf = 0.57, thin layer chromatography

[fluorescent silica gel plate developed with 50% methanol-50% benzene (by volume)].

Anal. calcd. for $C_{14}H_{20}N_2O_5 \cdot HCl$: C, 50.52; H, 6.36; N, 8.41 Found: C, 50.49; H, 6.69; N, 8.49

EXAMPLE 25

Preparation of 3-acetamidopropyl L-3-(3,4-dihydroxyphenyl)-2-methylalaninate hydrogen oxalate hydrate Thionyl chloride, 275 ml., is added to 250 g. of L-3-(3,4-dihydroxyphenyl)-2-methylalaninate sesquihydrate at 25° C. and the mixture is heated on the steam bath. After heating for two hours, the thick reaction mixture is diluted with 7.5 ml. dimethylformamide dissolved in 25 ml. of benzene and stirred on the steam bath until gas evolution ceases. 100 Ml. of benzene is added and the crude sulfurous acid ester is removed by filtration, washed with 100 ml. of benzene, 100 ml. of chloroform and 100 ml. of ether and dried under reduced pressure to give 280 g. of the sulfurous acid ester intermediate, m.p. 199° C. dec.

A mixture of 13.7 g. of the crude sulfurous acid ester intermediate, 24.98 g. (0.212 mole) of N-acetylpropanolamine and 2 g. of anhydrous dimethylformamide is stirred on the steam bath for 20 hours and cooled. The reaction mixture is washed with six 200 ml. portions of ethyl ether, four 200 ml. portions of methylene chloride and dried under reduced pressure. The semisolid material remaining is stirred with 200 ml. 20% ethanol-30% ethyl acetate (by volume), 20 ml. saturated sodium carbonate solution and 20 g. solid sodium carbonate. The organic extract is dried over anhydrous magnesium sulfate, filtered and the filtrate added to a solution of 3.2 g. oxalic acid in 50 ml. ethanol. Removal of solvents under reduced pressure is then accomplished and the product is precipitated by dissolving it in 50 ml. of ethanol and adding 500 ml. of ethyl ether. The product is again precipitated by dissolving in 50 ml. of ethanol and adding 500 ml. of ethyl acetate to give 3-acetamidopropyl L-3-(3,4-dihydroxypheny)-2-methylalaninate hydrogen oxalate hydrate, Rf = 0.45, thin layer chromatography [fluorescent silica gel plate developed with 25% methanol-75% chloroform (by volume)].

Anal. calcd. for $C_{15}H_{22}N_2O_5 \cdot C_2H_2O_4 \cdot H_2O$: C, 48.80; H, 6.26; N, 6.69 Found: C, 48.73; H, 6.85; N, 6.68

EXAMPLE 26

Preparation of 2-methylthioethyl L-3-(3,4-dihydroxyphenyl)-2-methylalaninate hydrogen oxalate Thionyl chloride, 275 ml., is added to 250 g. of L-3-(3,4-dihydroxyphenyl)-2-methylalaninate sesquihydrate at 25° C. and the mixture is heated on the steam bath. After heating for two hours, the thick reaction mixture is diluted with 7.5 ml. dimethylformamide in 25 ml. of benzene and stirred on the steam bath until gas evolution ceases. 100 Ml. of benzene is added and the crude sulfurous acid ester is removed by filtration, washed with 100 ml. of benzene, 100 ml. of chloroform and 100 ml. of ether and dried under reduced pressure to give 280 g. of the sulfurous acid ester intermediate, m.p. 199° C. dec.

A mixture of 30 g. of the crude sulfurous acid ester, 34.6 g. (0.375 mole) of 2-hydroxyethylmethylsulfide and 6 g. of anhydrous dimethylformamide is stirred on the steam bath for 28 hours and cooled. The reaction mixture is washed with four 100 ml. portions of ethyl ether and three 100 ml. portions of methylene chloride. The remaining material is stirred with 250 ml. of 20% ethanol-80% ethyl acetate (by volume), 30 ml. saturated sodium carbonate solution and 60 g. solid sodium carbonate and then filtered. The insoluble material is washed with three 250 ml. portions of 20% ethanol-80% ethyl acetate (by volume), combined with the first ethanol-ethyl acetate extract and dried over anhydrous magnesium sulfate. After filtering, solvents are removed under reduced pressure and the residue is chromatographed over silica gel. A total of 2.3 g. of product is eluted with a 25% methanol-75% chloroform (by volume) mixture. This product is converted to the oxalate salt by adding it to a solution of 1.3 g. of oxalic acid in 25 ml. of ethanol followed by precipitation with sufficient ethyl ether. After three more precipitations using ethanol to dissolve the product and ethyl ether to precipitate it, 300 mg. of the 2-methylthioethyl L-3-(3,4-dihydroxyphenyl)-2-methylalaninate hydrogen oxalate is obtained, homogeneous upon thin layer chromarography [fluorescent silica gel plate developed with 25% methanol-75% chloroform (by volume)] Rf = 0.83, m.p. 85°-90° C. dec.

Anal. calcd. for $C_{13}H_{19}NO_4S \cdot C_2H_2O_4$: C, 47.99; H, 5.64; N, 3.73 Found: C, 48.00; H, 6.10; N, 4.07

EXAMPLE 27

A. Preparation of D,L-3-(3,4-diphenylmethylenedioxyphenyl)-2-methylalanine hydrochloride A mixture of 38.6 g. (0.155 mole) of racemic-3-(3,4-dihydroxyphenyl)-2-methylalanine hydrochloride and 74 g. (0.312 mole) of dichlorodiphenylmethane is immersed with slow stirring in a preheated oil bath at 190° C. After reaction has started, the reaction mixture is stirred rapidly for six minutes at 190° C., removed from the hot oil bath and allowed to cool to 25° – 30° C. The crude product from 6 runs is combined, slurried with 2 l. of diethyl ether, filtered, washed with an additional 2 l. of diethyl ether and dried at 30° C. under 50 mm. pressure. The solid is recrystallized by dissolving the product in ethanol and adding ethyl acetate to precipitate D,L-3-(3,4-diphenylmethylenedioxyphenyl)-2-methylalanine hydrochloride.

B. Preparation of D,L-N-carbobenzyloxy-3-(3,4-diphenylmethylenedioxyphenyl)-2-methylalanine A mixture of 175 g. (0.425 mole) of racemic-3-(3,4-diphenylmethylenedioxyphenyl)-2-methylalaine hydrochloride, 1750 ml. of acetone and 1750 ml. of water is stirred under nitrogen at a temperature below 10° C. while the pH is adjusted to 12.0 by the slow addition of a 10% sodium hydroxide solution. Carbobenzyloxy chloride, 93 g. (0.545 mole) is added dropwise over 5 – 7 minutes to the reaction mixture at 20° – 30° C. accompanied by the simultaneous addition of a 10% sodium hydroxide solution to maintain a pH of 12.0 – 12.2. After addition of the carbobenzyloxy chloride is complete, the reaction mixture is stirred at 25° – 30° C. for 3 hours. Most of the acetone is then removed under reduced pressure at 25 to 35° C. to precipitate the sodium salt of the desired N-carbobenzyloxy derivative. The sodium salt is extacted into 1.5 l. of ethyl acetate, washed with 200 ml. of 5% sodium hydroxide solution and 200 ml. of a saturated sodium chloride solution and then dried over magnesium sulfate. After adding 17.5 g. of decolorizing carbon and filtering through a magnesium sulfate pad, solvents are removed under reduced pressure at 25° to 35° C. The residue is slurried two times with 1 l. of a 20% ethyl ether-80% hexane (by volume) solution and filtered to give the sodium salt of the desired N-carbobenzyloxy derivative. This sodium salt is dissolved in 1.5 l. of ethyl acetate, cooled to 10° C. and acidified to pH 2 with 6 N hydrochloric acid. The ethyl acetate extract is washed with 200 ml. of a saturated sodium chloride solution, dried over magnesium sulfate, filtered and concentrated under reduced pressure at 25 to 35° C. The N-carbobenzyloxy derivative is dried further at 25° - 30° C. and 0.2 - 0.3 mm. Hg to give D,L-N-carbobenzyloxy-3-(3,4-diphenylmethylenedioxyphenyl)-2-methyl-alanine.

C. Preparation of D,L-succinimidomethyl N-carbobenzyloxy-3-(3,4-diphenylmethylenedioxyphenyl)-2-methylalaninate A solution of 13.5 g. (0.0265 mole) of D,L-N-carbobenzyloxy-3-(3,4-diphenylmethylenedioxyphenyl)-2-methylalanine, 2.7 g. (0.027 mole) of triethylamine and 5.19 g. (0.029 mole) of N-bromomethylsuccinimide in 35 ml. of dry dimethylformamide is stirred at 25° - 30° C. for 16 hours. The reaction mixture is poured into 400 ml. of ice water and the product extracted into 200 ml. of a 50% chloroform-50% diethyl ether (by volume) mixture. The organic extract is washed with 50 ml. of a dilute (5%) sodium carbonate solution and 50 ml. of a saturated sodium chloride solution and then dried over anhydrous magnesium sulfate to remove water. After filtering and concentrating under reduced pressure, the residue is recrystallized. Recrystallization is accomplished by dissolving the product in ethanol and adding hexane to precipitate D,L-succinimidomethyl N-carbobenzyloxy-3-(3,4-diphenylmethylene-dioxyphenyl)-2-methylalaninate.

D. Preparation of D,L-succinimidomethyl 3-(3,4-dihydroxyphenyl)-2-methylalaninate hydrochloride hydrate A suspension of 6.6 g. (0.0106 mole) of racemic succinimidomethyl N-carbobenzyloxy-3-(3,4-diphenylmethylenedioxyphenyl)-2-methylalaninate in 180 ml. of absolute ethanol and 9 ml. of a 9.6 N ethanolic-anhydrous hydrogen chloride solution is hydrogenated with 3.3 g. of a 10% palladium-on-carbon catalyst as an initial pressure of 30 p.s.i. until hydrogen uptake is complete. After removal of catalyst by filtration, the filtrate is concentrated under reduced pressure. The residue is extracted with 50 ml. of benzene and then 50 ml. of ethyl acetate. The insoluble solid is then shaken with 50 ml. of a 10% ethanol-90% ethyl acetate (by volume) mixture and 10 ml. of a saturated sodium carbonate solution. After filtration, the filtrate is dried over anhydrous magnesium sulfate, filtered and concentrated under reduced pressure to give D,L-succinimidomethyl 3-(3,4-dihydroxyphenyl)-2-methyl-alaninate as the base.

E. Preparation of succinimidomethyl L-3-(3,4-dihydroxyphenyl)-2-methylalaninate hydrochloride hydrate via recrystallization of diastereomeric salts A solution of 0.47 g. (3.1 mmole) of (−) tartaric acid in 10 ml. of a 50% absolute ethanol-50% ethyl acetate (by volume) solution is added under nitrogen at 20° - 25° C. to a solution of 1.0 g. (3.1 mmole) of D,L-succinimidomethyl 3-(3,4-dihydroxyphenyl)-2-methylalaninate in 10 ml. of absolute ethanol. After warming the solution to 40° - 60° C., ethyl acetate is added to incipient cloudiness and then cooled slowly to 25° C. and finally stored at 5° - 10° C. for 12 hours. The insoluble crude tartrate salt is removed by filtration and dried at 20° - 25° C. and 0.2 - 0.5 mm. pressure. This recrystallization procedure is repeated until the melting point and optical rotation of the tartrate salt are essentially constant.

The mother liquor from the initial crystallization is concentrated at 15 - 20 mm. and 40° - 50° C. The residue is shaken with 25 ml. of a 10% ethanol-90% ethyl acetate (by volume) mixture and 10 ml. of a saturated sodium carbonate solution. After filtration, the filtrate is dried over anhydrous magnesium sulfate, filtered and concentrated at 15 - 20 mm. and 40° C. to a gun. The residue is dissolved in 5 ml. of absolute ethanol and added under nitrogen to a solution of 0.3 g. of (+) tartaric acid in 10 ml. of a 50% absolute ethanol-50% ethyl acetate (by volume) solution. After warming the solution to 40 - 60° C., ethyl acetate is added to incipient cloudiness and then cooled slowly to 25° C. and then stored at 5° - 10° C. for 14 hours. The insoluble crude tartrate salt is removed by filtration. Repetition of this recrystallization procedure gives the other optical antipode of succinimidomethyl 3-(3,4-dihydroxyphenyl)-2-methylalaninate as the tartrate salt.

The optically active tartrate salts are converted to the optically active hydrochloride salts by the following method. The tartrate salt of succinimido L-3-(3,4-dihydroxypheny)-2-methylalaninate is shaken with 50 ml. of a 10% ethanol-90% ethyl acetate (by volume) mixture and 10 ml. of a saturated sodium carbonate solution. After filtration, the filtrate is dried over anhydrous magnesium sulfate, filtered and concentrated under reduced pressure. The residue is redissolved in 25 ml. of absolute ethanol, treated with 5 ml. of a 9.6 N ethanolic-anhydrous hydrogen chloride solution and concentrated under reduced pressure to give succinimidomethyl L-3-(3,4-dihydroxyphenyl)-2-methylalaninate hydrochloride hydrate, homogeneous upon thin layer chromatography [fluorescent silica gel plate, 30% methanol-70% benzene (by volume) solvent] with an observed Rf = 0.5.

EXAMPLE 28

Resolution of racemic pivaloyloxymethyl 3-(3,4-dihydroxyphenyl)-2-methylalaninate by direct recrystallization Racemic pivaloyloxymethyl 3-(3,4-dihydroxyphenyl)-2-methylalaninate hydrochloride is prepared as in Example 23.

Thirty grams of racemic pivaloyloxymethyl 3-(3,4-dihydroxyphenyl)-2-methylalaninate hydrochloride are slurried at 35° C. in 100 ml. of 1.0 N hydrochloric acid. The excess solids are filtered. The saturated solution is then seeded at 35° C. with pivaloyloxymethyl D-3-(3,4-dihydroxyphenyl)-2-methylalaninate hydrochloride hydrate. The mixture is cooled to 20° C. in 30 minutes and allowed to stand at 20° C. for 0.5 hour. The separated material is isolated by filtration, washed twice with 5 ml. cold water and dried at 0.1 - 0.5 mm. and 20° - 25° C. for 20 hours to give pivaloyloxymethyl D-3-(3,4-dihydroxyphenyl)-2-methylalaninate hydrochloride hydrate.

The mother liquor from the preceding step is heated to 35° C. and is seeded at 35° C. with pivaloyloxymethyl L-3-(3,4-dihydroxyphenyl)-2-methylalaninate hydrochloride. The mixture is then cooled to 20° C. over 30 minutes and allowed to stand at 20° C. for 0.5 hour. The precipitated material is isolated by filtration, washed twice with 5 ml. cold water and dried at 0.1 - 0.5 mm. and 20° -25° C. for 20 hours to give pivaloyloxymethyl L-3-(3,4-dihydroxyphenyl)-2-methylalaninate hydrochloride hydrate.

EXAMPLE 29

A. Preparation of α-succinimidoethyl L-3-(3,4-dihydroxyphenyl)-2-methylalaninate hydrochloride dihydrate (β-isomer) by fractional crystallization Ten grams of α-succinimidoethyl L-3-(3,4-dihydroxyphenyl)-2-methylalaninate hydrochloride (α- and β-isomer mixture) of Example 2 are dissolved in 50 ml. warm 95% ethanol (5% water), diluted to incipient cloudiness with anhydrous ether, seeded and scratched to induce crystallization. After cooling at 5° - 10° C. for 12 hours, the precipitated solid is collected and dried at 70° C. Additional similar recrystallizations from 95% ethanol-5% water-ethyl ether (by volume) give material melting at 123° - 126° C. (dec.). A final recrystallization from 95% ethanol affords α-succinimidoethyl L-3-(3,4-dihydroxyphenyl)-2-methylalaninate hydrochloride dihydrate (β-isomer) as the dihydrate melting at 129° - 131° C. (dec.) (dried at 70° C. overnight), homogeneous upon thin layer chromatography [fluorescent silica gel plate, 50% methanol-50% benzene (by volume) solvent], Rf = 0.7.

B. Preparation of α-succinimidoethyl L-3-(3,4-dihydroxyphenyl)-2-methylalaninate hydrochloride hydrate (α-isomer)

The mother liquor from the first crystallization of the β-isomer of a α-succinimidoethyl L-3-(3,4-dihydroxyphenyl)-2-methylalaninate hydrochloride hydrate which is rich in the corresponding α-isomer is concentrated at 15 - 20 mm. and 40° - 45° C. The residue is dissolved in 20 ml. warm 95% ethanol (5% water), diluted to incipient cloudiness with ethyl acetate, seeded and scratched to precipitate the enriched α-isomer of α-succinimidoethyl L-3-(3,4-dihydroxyphenyl)-2-methylalaninate hydrochloride hydrate. Additional precipitations from 95% ethanol (5% water) and ethyl acetate gives the α-isomer as the ethyl acetate solvate, Rf = 0.7 [thin layer chromatography, fluorescent silica gel plate, 50% methanol-50% benzene (by volume) solvent].

EXAMPLE 30

Preparation of pivaloyloxymethyl L-3-(3,4-dihydroxyphenyl)-2-methylalaninate hydrochloride A solution of 0.95 g. (4.0 mmole) of L-3-(3,4-dihydroxphenyl)-2-methylalanine sesquihydrate and 0.61 g. (4.06 mmole) of pivaloyloxymethyl chloride in 5 ml. dimethylsulfoxide is stirred at 20° - 25° C. or 23 hours. The solution is diluted with 10 ml. distilled water and passed through a column containing 5 g. of weakly basic anion exchange resin on the base cycle. After elution with water fractions, the fractions giving a positive ferric chloride test are combined and added to a column of 3 g. of weakly acidic cation exchange resin on the acid cycle. Unreacted L-3-(3,4-dihydroxyphenyl)-2-methylalanine is eluted with distilled water until a negative ferric chloride test is obtained, the ester is then eluted with 1 N acetic acid. The ester fraction, 50 ml. (pH 3.2), is acidified to pH 2.0 with 1 N hydrochloric acid and lyophilized at 0.1 - 0.3 mm. for 20 hours to give pivaloyloxmethyl L-3-(3,4-dihydrophenyl)-2-methyl-alaninate hydrochloride as the acetic acid solvate.

Anal. calcd. for $C_{16}H_{23}NO_6.HCl.1/3HC_2H_4O_2$: C, 52.11; H, 6.69; N, 3.58; Found: C, 52.11; H, 6.49; N, 3.73.

EXAMPLE 31

Preparation of α-succinimidoethyl L-3-(3,4-dihydroxyphenyl)-2-methylalaninate hydrochloride A solution of 0.95 g. (4.0 mmole) of L-3-(3,4-dihydroxyphenyl)-2-methylalanine sesquihydrate and 0.65 g. (4.0 mmole) of N-(α-chloroethyl)-succinimide in 5 ml. dimethylsulfoxide is stirred at 20° - 25° C. for 23 hours. The solution is diluted with 10 ml. distilled water and passed through a column containing 5 g. of weakly basic anion exchange resin on the basic cycle. After elution with water fractions, the fractions giving a positive ferric chloride test are combined and added to a column of 3 g. of a weakly acidic cation exchange resin on the acid cycle. Unreacted L-3-(3,4-dihydroxyphenyl)-2-methylalanine is eluted with distilled water until a negative ferric chloride test is obtained and the ester is then eluted with 1 N acetic acid. The ester fraction, 55 ml. (pH 3.2), is treated with 1 N hydrochloric acid to pH 2.0 and lyophilized at 0.1 - 0.3 mm. for 20 hours to give α-succinimidoethyl L-3-(3,4-dihydroxyphenyl)-2-methylalaninate hydrochloride acetic acid solvate.

Anal. calcd. for $C_{16}H_{20}N_2O_6.HCl.1/3C_2H_4O_2$: C, 50.96; H, 5.73; N, 7.13 Found: C, 50.48; H, 6.13; N, 6.77

EXAMPLE 32

Preparation of 3-acetamidopropyl L-3-(3,4-dihydroxyphenyl)-2-methylalaninate hydrogen oxalate hydrate Thionyl chloride, 275 ml., is added to 250 g. of L-3-(3,4-dihydroxyphenyl)-2-methylalaninate sesquihydrate at 25° C. and the mixture is heated on the steam bath. After heating for two hours, the thick reaction mixture is diluted with 7.5 ml. dimethylformamide dissolved in 25 ml. of benzene and stirred on the steam bath until gas evolution ceases. 100 Ml. of benzene is added and the crude sulfurous acid ester is removed by filtration, washed with 100 ml. of benzene, 100 ml. of chloroform and 100 ml. of ether and dried under reduced pressure to give 280 g. of the sulfurous acid ester intermediate, m.p. 199° C. dec.

A mixture of 13.7 g. of the crude sulfurous acid ester intermediate, 24.98 g. (0.212 mole) of N-acetylpropanolamine and 2 g. of anhydrous dimethylformamide is stirred on the steam bath for 20 hours and cooled. The reaction mixture is washed with six 200 ml. portions of ethyl ether, four 200 ml. portions of methylene chloride and dried under reduced pressure. The semisolid material remaining is stirred with 200 ml. 20% ethanol-80% ethyl acetate (by volume), 20 ml. saturated sodium carbonate solution and 20 g. solid sodium carbonate. The organic extract is dried over anhydrous magnesium sulfate, filtered and the filtrate added to a solution of 3.2 g. oxalic acid in 50 ml. ethanol. Removal of solvents under reduced pressure is then accomplished and the product is precipitated by dissolving it in 50 ml. of ethanol and adding 500 ml. of ethyl ether. The product is again precipitated by dissolving in 50 ml. of ethanol and adding 500 ml. of ethyl acetate to give 3-acetamidopropyl L-3-(3,4-dihydroxyphenyl)-2-methylalaninate hydrogen oxalate hydrate, Rf = 0.45, thin layer chromatography [fluorescent silica gel plate developed with 25% methanol-75% chloroform (by volume)].

Anal. calcd. for $C_{15}H_{22}N_2O_5.C_2H_2O_4.H_2O$: C, 48.80; H, 6.26; N, 6.69 Found: C, 48.73; H, 6.85; N, 6.68

EXAMPLE 33

Preparation of 2-acetamidoethyl L-3-(3,4-dihydroxyphenyl)-2methylalaninate hydrochloride A slurry of 88.3 g. (0.30 mole) of L-3-(3,4-dihydroxyphenyl)-2-methylalanine hydrochloride ethanol solvate (by concentration of an ethanolic solution of the hydrochloride under reduced pressure) and 146.4 g. (1.42 mole) of N-acetylethanolamine, under nitrogen, is warmed to 104° - 108° C. Thionyl chloride, 84.8 g. (0.713 mole) is added over 15 minutes with stirring. The reaction mixture foams vigorously during the addition. After addition is complete, the reaction mixture is stirred at 104° - 108° C. for 18 hours. Additional thionyl chloride, 42.4 g. (0.357 mole) is added over seven minutes. The reaction mixture is allowed to stir at 104° - 108° C. for another 3½ hours, then cooled to 30° C. and concentrated under reduced pressure to yield a viscous oil. This oil is slurried with 100 ml. of chloroform and the chloroform removed under reduced pressure. This is repeated three times and then the oil is washed with 100 ml. of benzene which is decanted. The residue is dissolved in 700 ml. of isopropanol and added to 6 l. of ethyl ether. The precipitate which forms is washed with 500 ml. of ethyl ether and shaken with 6 l. of 10% ethanol-90% ethyl acetate (by volume), 150 ml. of saturated sodium carbonate solution and 100 g. of sodium carbonate. The organic extract is dried over anhydrous magnesium sulfate, filtered and concentrated under reduced pressure to give the free base of the acetamidoethyl ester. This base is treated with 15 g. of fumaric acid in 300 ml. of isopropanol and the fumarate salt precipitated by adding sufficient ethyl ether. The fumarate salt is precipitated once more from isopropanol by adding sufficient ethyl ether and then converted back to the free base as before by shaking with 200 ml. of 10% ethanol-90% ethyl acetate (by volume), 20 ml. of saturated sodium carbonate solution and 20 g. solid sodium carbonate. The free base is converted to the hydrochloride salt by dissolving in 100 ml. of absolute ethanol, adding 10 ml. 9.6 N HCl and precipitated by addition to 1 l. of ethyl ether. After three precipitations from ethanol-ethyl ether as carried out above, 2-acetamidoethyl L-3-(3,4-dihydroxyphenyl)-2-methylalaninate hydrochloride is obtained, Rf = 0.57, thin layer chromatography [fluorescent silica gel plate developed with 50% methanol-50% benzene (by volume)].

Anal. calcd. for $C_{14}H_{20}N_2O_5.HCl$: C, 50.52; H, 6.36; N, 8.41 Found: C, 50.49; H, 6.69; N, 8.49

EXAMPLE 34

A. Preparation of L-3-(3,4-diacetoxyphenyl)-2-methylalanine hydrochloride

To a mixture of 320 ml. glacial acetic acid and 24 ml. acetyl chloride is added in one portion 69.4 g. (0.291 mole) of L-3-(3,4-dihydroxyphenyl)-2-methylalanine sesquihydrate. The temperature of the reaction mixture rises to approximately 50° C. and a clear solution results. At this temperature, an additional 85 ml. of acetyl chloride is added over 10 minutes. The resulting clear, pale yellow solution is allowed to stand at 20° - 25° C. for 14 hours. Anhydrous ethyl ether, 400 ml., is added over 15 minutes. When addition is almost complete, a white solid begins to precipitate. The mixture is stirred at 20° - 25° C. for 30 minutes, at 5° - 10° C. for 1 hour and then cooled at −10° C. for 2 hours. The solid is removed by filtration, suspended in 150 ml. of 30% acetic acid-70% ethyl ether (by volume), filtered and washed with 500 ml. ethyl ether. After drying at 70° C. for 2 hours, 83.7 g. (88%) of L-3-(3,4-diacetoxyphenyl)-2-methylalanine hydrochloride, m.p. 196.0° - 197.0° C., is obtained.

B. Preparation of L-3-(3,4-diacetoxyphenyl)-2-methylalanyl chloride hydrochloride A mixture of 6.60 g. (0.020 mole) of L-3-(3,4-diacetoxyphenyl)-2-methylalanine hydrochloride and 40 ml. thionyl chloride is stirred at 60° C. for 2 hours until solution is complete. Excess thionyl chloride is removed at 15 - 20 mm. and 40° - 50° C. Methylene chloride, 50 ml., is added and the mixture is reconcentrated at 15 - 20 mm. and 40° - 50° C. This is repeated once more with another 50 ml. of methylene chloride. After drying at 0.2 - 0.5 mm. and 40° C. for 30 minutes, L-3-(3,4-diacetoxyphenyl)-2-methylalanyl chloride is obtained.

C. Preparation of succinimidomethyl L-3-(3,4-dihydroxyphenyl)-2-methylalaninate hydrochloride hydrate A solution of 3.50 g. (10 mmole) of L-3-(3,4-diacetoxyphenyl)-2-methylalanyl chloride hydrochloride in 20 ml. chloroform is added to a solution of 3.87 g. (30 mmole) of N-hydroxymethylsuccinimide in 20 ml. chloroform at 25° C. After stirring at reflux for 20 hours, most of the chloroform is removed at 15 - 20 mm. and 30° - 40° C. The residue is diluted with 10 ml. of 1 N hydrochloric acid and extracted with two 20 ml. portions of ethyl ether. The aqueous extract is stirred under nitrogen at 20° - 25° C. for 5 hours. After lyophilization at 0.1 - 0.3 mm. for 20 hours, the residue is treated with 50 ml. of a 10% ethanol-90% ethyl acetate (by volume) solution, 5 ml. of a saturated sodium carbonate solution and 5 g. of solid sodium carbonate. After filtration, the filtrate is dried over anhydrous magnesium sulfate, filtered and concentrated at 15 - 20 mm. and 30° - 40° C. The residue is redissolved in 25 ml. of absolute ethanol, treated with 5 ml. of a 9.6 N ethanolic-anhydrous hydrogen chloride solution and concentrated under reduced pressure to give succinimidomethyl L-3-(3,4-dihydroxyphenyl)-2-methylalaninate hydrochloride hydrate, homogeneous upon thin layer chromatography [fluorescent silica gel plate, 30% methanol-70% benzene (by volume) solvent] with an observed Rf = 0.5.

EXAMPLE 35

A. Preparation of the N-carboxyanhydride of L-3-(3,4-dihydroxyphenyl)-2-methylalanine Phosgene gas is bubbled through a mixture of 9.0 g. (0.038 mole) of L-3-(3,4-dihydroxyphenyl)-2-methylalanine sesquihydrate in 500 ml. tetrahyrofuran for 25 minutes until the solution is saturated. During the addition, the temperature of the reaction mixture rises to 45° C. The solution is stirred with nitrogen gas bubbling through for an additional 50 minutes. Insoluble material is removed by filtering through a diatomaceous earth pad and the filtrate is concentrated to an oil at 15 – 20 mm. pressure and 30° – 35° C. The residue is dissolved in 75 ml. ethyl acetate and hexane is added to the cloudpoint. After cooling for several days at 0° – 5° C., the precipitated solid is removed by filtration and dried at 0.1 – 0.3 mm. pressure and 25° C. to give the N-carboxyanhydride of L-3-(3,4-dihydroxyphenyl)-2-methylalanine.

B. Preparation of succinimidomethyl L-3-(3,4-dihydroxyphenyl)-2-methylalaninate hydrochloride hydrate A solution of 2.37 g. (10 mmole) of the N-carboxyanhydride of L-3-(3,4-dihydroxyphenyl)-2-methylalanine and 1.29 g. (10 mmole) of N-hydroxymethylsuccinimide is heated at reflux until all of the N-carboxyanhydride has reacted. After concentrating at 15 – 20 mm. pressure and 30° – 40° C., the residue is extracted with 50 ml. of benzene and then 50 ml. of ethyl acetate. The insoluble solid is then shaken with 50 ml. of a 10% ethanol-90% ethyl acetate (by volume) mixture and 10 ml. of a saturated sodium carbonate solution. After filtration, the filtrate is dried over anhydrous magnesium sulfate, filtered and concentrated under reduced pressure. The residue is redissolved in 25 ml. of absolute ethanol, treated with 5 ml. of a 9.6 N ethanolic-anhydrous hydrogen chloride solution and concentrated under reduced pressure to give succinimidomethyl L-3-(3,4-dihydroxyphenyl)-2-methylalaninate hydrochloride hydrate, homogeneous upon thin layer chromatography [fluorescent silica gel plate, 30% methanol-70% benzene (by volume) solvent] with an observed Rf = 0.5.

EXAMPLE 36

A. Preparation of L-3-(3,4-diphenylmethylenedioxyphenyl)-2-methylalanine hydrochloride A mixture of 19.3 g. (0.0777 mole) of L-3-(3,4-dihydroxyphenyl)-2-methylalanine hydrochloride and 37 g. (0.156 mole) of dichlorodiphenylmethane is immersed with slow stirring in a preheated oil bath at 190° C. After reaction has started, as evidenced by vigorous gas evolution, the reaction mixture is stirred rapidly for 6 minutes at 190° C., removed from the hot oil bath and allowed to cool to 25° – 30° C. The crude product from 12 runs is combined, slurried with 3 l. of diethyl ether, filtered, washed with an additional 2 l. of diethyl ether and dried at 30° C. under 50 mm. pressure. Recrystallization is accomplished by dissolving the product in ethanol and adding ethyl acetate to precipitate the product. The procedure gives 255 g. (66.4%) of L-3-(3,4-diphenylmethylenedioxyphenyl)-2-methylalanine hydrochloride, m.p. 267° – 268° C. dec.

B. Preparation of α-succinimidoethyl L-3-(3,4-diphenylmethylenedioxyphenyl)-2-methylalaninate A solution of 1.4 g. (4.0 mmole) of L-3-(3,4-diphenylmethylenedioxyphenyl)-2-methylalanine and 0.65 g. (4.0 mmole) of N-(α-chloroethyl)-succinimide in 5 ml. dimethylsulfoxide is stirred at 20° – 25° C. for 23 hours. Water, 150 ml., is added followed by a saturated sodium carbonate solution until a pH of 8 is obtained. The product is extracted into 500 ml. of ethyl ether which is then washed with four 25 ml. portions of water, dried over anhydrous magnesium sulfate and filtered. Concentration at 15 – 20 mm. and 35° – 40° C. gives crude α-succinimidoethyl L-3-(3,4-diphenylmethylenedioxyphenyl)-2-methylalaninate of sufficient purity for use in the next step.

C. Preparation of α-succinimidoethyl L-3-(3,4-dihydroxyphenyl)-2-methylalaninate hydrochloride A suspension of 1.0 g. (2.0 mmole) of α-succinimidoethyl L-3-(3,4-diphenylmethylenedioxyphenyl)-2-methylalaninate in 25 ml. of 25% absolute ethanol-75% ethyl acetate (by volume) solution is hydrogenated with 1.0 g. of 10% palladium-on-carbon catalyst at an initial pressure of 40 p.s.i. and room temperature for 23 hours. The catalyst is filtered and the filtrate evaporated under reduced pressure at 30° to 40° C. The residue is dissolved in 50 ml. of 10% ethanol-90% ethyl acetate (by volume) solution and stirred with 5 ml. of saturated sodium carbonate solution and approximately 5 g. of anhydrous sodium carbonate for 10 minutes. After filtration, the filtrate is dried over anhydrous magnesium sulfate, filtered and evaporated to dryness under reduced pressure. The residue is dissolved in 20 ml. of dry chloroform, the solution is cooled in an ice bath and saturated with hydrogen chloride gas for 15 minutes. The solid is collected, washed by suspension in 25 ml. of anhydrous ether three times and then slurried in 25 ml. of ethyl acetate under $N_2$ in a stoppered flask at room temperature overnight. The insoluble solid is removed by filtration, stirred with 30 ml. hexane for 2 hours and dried in a vacuum desiccator over $CaCl_2$ to give α-succinimidoethyl L-3-(3,4-dihydroxyphenyl)-2-methylalaninate hydrochloride as a mixture of α- and β-isomers, observed Rf = 0.7 upon thin layer chromatography [fluorescent silica gel plate, 50% methanol-50% benzene (by volume) solvent].

EXAMPLE 37

A. Preparation of L-3-(3,4-diacetoxyphenyl)-2-methylalanine hydrochloride

To a mixture of 320 ml. glacial acetic acid and 24 ml. acetyl chloride is added in one portion, 69.4 g. (0.291 mole) of L-3-(3,4-dihydroxyphenyl)-2-methylalanine sesquihydrate. The temperature of the reaction mixture rises to approximately 50° C. and a clear solution results. At this temperature, an additional 85 ml. of acetyl chloride is added over 10 minutes. The resulting clear, pale yellow solution is allowed to stand at 20° – 25° C. for 14 hours. Anhydrous ethyl ether, 400 ml., is added over 15 minutes. When addition is almost complete, a white solid begins to precipitate. The mixture is stirred at 20° – 25° C. for 30 minutes, at 5° – 10° C. for 1 hour and then cooled at −10° C. for 2 hours. The solid is removed by filtration, suspended in 150 ml. of 30% acetic acid-70% ethyl ether (by volume), filtered and washed with 500 ml. ethyl ether. After drying at 70° C. for 2 hours, 83.7 g. (88%) of L-3-(3,4-diacetoxyphenyl)-2-methylalanine hydrochloride, m.p. 196.0° – 197.0° C., is obtained.

B. Preparation of α-succinimidoethyl L-3-(3,4-diacetoxyphenyl)-2-methylalaninate hydrochloride A solution of 1.66 g. (5 mmole) of L-3-(3,4-diacetoxyphenyl)-2-methylalanine hydrochloride, 0.51 g. (5 mmole) of triethylamine and 0.81 g. (5 mmole) N-(α-chloroethyl)-succinimide in 5 ml. of dimethyl sulfoxide is stirred at 20° – 25° C. for 20 – 24 hours. Dimethyl sulfoxide is removed by stirring with 20 ml. ethyl ether for several minutes and then decanting off the ethyl ether. This extraction process is carried out there times. The residue is dissolved in 10 ml. of absolute ethanol and the product precipitated by the addition of excess ethyl ether. This precipitation process is repeated two more times to give pure α-succinimidoethyl L-3-(3,4-diacetoxyphenyl)-2-methylalaninate hydrochloride.

EXAMPLE 38

Preparation of α-succinimidoethyl L-3-(3,4-dihydroxyphenyl)-2-methylalaninate hydrochloride A solution of 1.8 g. (3.94 mmole) of α-succinimidoethyl L-3-(3,4-diacetoxyphenyl)-2-methylalaninate hydrochloride (of Example 37) in 10 ml. of 1 N hydrochloric acid is stirred under nitrogen at 20° – 25° C. for 5 hours. After lyophilization at 0.1 – 0.3 mm. for 20 hours, the residue is treated with 50 ml. of a 10% ethanol-90% ethyl acetate (by volume) solution, 5 ml. of a saturated sodium carbonate solution and 5 g. of solid sodium carbonate. After filtration, the filtrate is dried over anhydrous magnesium sulfate, filtered and evaporated to dryness under reduced pressure. The residue is dissolved in 20 ml. of dry chloroform, the solution is cooled in an ice bath and saturated with hydrogen chloride gas for 15 minutes. The solid is collected, washed by suspension in 25 ml. of anhydrous ethyl ether three times and then slurried in 25 ml. of ethyl acetate under N₂ in a stoppered flask at room temperature overnight. The α-succinimidoethyl L-3-(3,4-dihydroxyphenyl)-2-methylalaninate hydrochloride is collected and dried in a vacuum desiccator over CaCl₂ to give the hydrochloride as a mixture of α- and β-isomers, observed Rf = 0.7 upon thin layer chromatography [fluorescent silica gel plate, 50% methanol-50% benzene (by volume) solvent].

EXAMPLE 39

Preparation of N-(1-chloroethyl)-maleimide

Stannic chloride, 5.20 g. (0.020 mole) is added to a solution of 49.2 g. (0.40 mole) of n-vinylmaleimide in 1 l. of carbon tetrachloride and the mixture is stirred while saturating with hydrogen chloride for 6 hours at 20° – 30° C. After 24 hours, the mixture is resaturated with hydrogen chloride for 1.5 hours. At the end of 48 hours, the solution is decanted and the gummy residue is washed with ten 100 ml. portions of carbon tetrachloride. The combined extracts are slurried with 10 g. of diatomaceous earth, filtered and the filtrate concentrated under reduced pressure to approximately 400 ml. The N-(1-chloroethyl)-maleimide is filtered and dried at 20° – 30° C.

B. Preparation of α-maleimidoethyl L-3-(3,4-dihydroxyphenyl)-2-methylalaninate hydrochloride A solution of 0.95 g. (4.0 mmole) of L-3-(3,4-dihydroxyphenyl)-2-methylalanine sesquihydrate and 0.64 g. (4.0 mmole) of N-(α-chloroethyl)-maleimide in 5 ml. dimethylsulfoxide is stirred at 20° – 25° C. for 23 hours. The solution is diluted with 10 ml. distilled water and passed through a column containing 5 g. of weakly basic anion exchange resin on the basic cycle. After elution with water fractions, the fractions giving a positive ferric chloride test are combined and added to a column of 3 g. of a weakly acidic cation exchange resin on the acid cycle. Unreacted L-3-(3,4-dihydroxyphenyl)-2-methylalanine is eluted with distilled water until a negative ferric chloride test is obtained and the ester is then eluted with 1 N acetic acid. The ester fraction, 55 ml. (pH 3.2), is treated with 1 N hydrochloric acid to pH 2.0 and lyophilized at 0.1 – 0.3 mm. for 20 hours to give α-maleimidoethyl L-3-(3,4-dihydroxyphenyl)-2-methylalaninate hydrochloride.

C. Preparation of α-succinimidoethyl L-3-(3,4-dihydroxyphenyl)-2-methylalaninate hydrochloride A solution of 1.0 g. (2.7 mmole) of α-maleimidoethyl L-3-(3,4-dihydroxyphenyl)-2-methylalaninate hydrochloride in 25 ml. absolute ethanol is hydrogenated with 1.0 g. of 10% palladium-on-carbon catalyst at atmospheric pressure and 25° C. until one equivalent of hydrogen is taken up. The catalyst is filtered and the filtrate evaporated under reduced pressure at 30° to 40° C. The residue is dissolved in 50 ml. of 10% ethanol-90% ethyl acetate (by volume) solution and stirred with 5 ml. of saturated sodium carbonate solution and approximately 5 g. of anhydrous sodium carbonate for 10 minutes. After filtration, the filtrate is dried over anhydrous magnesium sulfate, filtered and evaporated to dryness under reduced pressure. The residue is dissolved in 20 ml. of dry chloroform, the solution is cooled in an ice bath and saturated with hydrogen chloride for 15 minutes. The solid is collected, washed by suspension in 25 ml. of anhydrous ether three times and then slurried in 25 ml. of ethyl acetate under N₂ in a stoppered flask at 20° – 25° C. overnight. The insoluble solid is removed by filtration, stirred with 30 ml. hexane for 2 hours and dried in a vacuum desiccator over CaCl₂ to give α-succinimidoethyl L-3-(3,4-dihydroxyphenyl)-2-methylalaninate hydrochloride as a mixture of α- and β-isomers, observed Rf = 0.7 upon thin layer chromatography [fluorescent silica gel plate, 50% methanol-50% benzene (by volume) solvent].

EXAMPLE 40

A. Preparation of α-chloroethyl 3-chloro-2,2-dimethylpropionate

Zinc chloride, 400 mg. is fused at 0.2 – 0.5 mm. pressure and cooled to 25° – 30° C. under nitrogen. 3-Chloro-2,2-dimethylpropionylchloride, 62 g. (0.40 mole) is added to the fused zinc chloride followed by acetaldehyde, 19.2 g. (0.44 mole). During addition of the acetaldehyde, which is done as rapidly as possible, the reaction mixture is stirred and cooled to prevent loss of acetaldehyde due to the exothermic nature of the reaction. After heating at reflux for 1 hour, distillation gives α-chloroethyl 3-chloro-2,2-dimethylpropionate.

B. Preparation of α-(3-chloro-2,2-dimethylpropionyloxy)-ethyl L-3-(3,4-dihydroxyphenyl)-2-methylalaninate hydrochloride A solution of 0.95 g. (4.0 mmole) of L-3-(3,4-dihydroxyphenyl)-2-methylalanine sesquihydrate and 0.81 g. (4.06 mmole) of α-chloroethyl 3-chloro-2,2-dimethylpropionate in 5 ml. dimethylsulfoxide is stirred at 20° - 25° C. for 23 hours. The solution is diluted with 10 ml. distilled water and passed through a column containing 5 g. of weakly basic anion exchange resin on the base cycle. After elution with water fractions, the fractions giving a positive ferric chloride test are combined and added to a column of 3 g. of weakly acidic cation exchange resin on the acid cycle. Unreacted L-3-(3,4-dihydroxyphenyl)-2-methylalanine is eluted with distilled water until a negative ferric chloride test is obtained, the ester is then eluted with 1 N acetic acid. The ester fraction, 50 ml. (pH 3.2), is acidified to pH 2.0 with 1 N hydrochloric acid and lyophilized at 0.1 - 0.3 mm. for 20 hours to give α-(3-chloro-2,2-dimethylpropionyloxy)-ethyl L-3-(3,4-dihydroxyphenyl)-2-methylalaninate hydrochloride as the acetic acid solvate.

C. Preparation of α-pivaloyloxyethyl L-3-(3,4-dihydroxyphenyl)-2-methylalaninate hydrochloride A solution of 1.5 g. (3.66 mmole) of α-(3-chloro-2,2-dimethylpropionyloxy)-ethyl L-3-(3,4-dihydroxyphenyl)-2-methylalaninate hydrochloride in 20 ml. absolute ethanol is hydrogenated with 1.0 g. of a 10% palladium-on-carbon catalyst at 20° - 25° C. and atmospheric pressure until one equivalent of hydrogen is taken up. After removing catalyst by filtration, ethanol is removed at 15 - 20mm. and 30° - 35° C. The residue is dissolved in 40 ml. ethyl acetate, stirred briefly with a mixture of 2 g. of solid sodium carbonate and 2 ml. saturated sodium carbonate solution and dried over anhydrous magnesium sulfate. After filtering, 1 ml. of 9.6 N ethanolic-anhydrous hydrogen chloride is added and the solution concentrated under reduced pressure to dryness. Further drying at 65° C. and 0.2 mm. pressure gives the α-pivaloyloxyethyl ester hydrochloride.

EXAMPLE 41

A. Preparation of benzyl succinamate

A mixture of 23.4 g. (0.20 mole) of succinamic acid, 25.4 g. (0.20 mole) of benzyl chloride, 20.2 g. (0.20 mole) triethylamine and 250 ml. dimethylformamide is stirred at 95° C. for 20 hours. The reaction mixture is diluted with 500 ml. water and the product extracted into two 200 ml. portions of ethyl ether. The combined ether extracts are washed with two 50 ml. portions of saturated sodium bicarbonate solution, then two 50 ml. portions of water and dried over anhydrous magnesium sulfate. After filtering, the solution is concentrated at 15 - 20 mm. and 40° C. to give benzyl succinamate.

B. Preparation of benzyl N-hydroxymethylsuccinamate

To a stirred solution of 20.7 g. (0.10 mole) of benzyl succinamate in 150 ml. ethyl acetate at 25° C. is added 3.0 g. of paraformaldehyde and 1 ml. of a 20% (by weight) solution of ethanolic potassium hydroxide. After stirring at 25° C. for 20 hours, hexane is added to the cloudpoint and the mixture is cooled at 5° C. for 24 hours. Solvents are decanted off and the residue is washed with 25 ml. hexane to give benzyl N-hydroxymethylsuccinamate.

C. Preparation of benzyl N-chloromethylsuccinamate

A solution of 24.2 g. (0.10 mole) of benzyl N-hydroxymethylsuccinamate and 28.9 g. (0.11 mole) of triphenylphosphine in 500 ml. carbon tetrachloride is stirred at reflux for 12 hours. After filtering and washing the precipitate with benzene, the organic solvents are removed at 15 - 20 mm. and 30° - 40° C. to give benzyl N-chloromethylsuccinamate of sufficient purity for use in the next step.

D. Preparation of benzylsuccinamidomethyl L-N-carbobenzyloxy-3-(3,4-diphenylmethylenedioxyphenyl)-2-methylalanine A solution of 10.2 g. (0.020 mole) of L-N-carbobenzyloxy-3-(3,4-diphenylmethylenedioxyphenyl)-2-methylalanine, 2.02 g. (0.020 mole) of triethylamine and 5.12 g. (0.020 mole) of benzyl N-chloromethylsuccinamate in 20 ml. dimethylformamide is stirred at 70° C. for 5 hours, then at 20° - 30° C. for 5 hours and finally poured into 200 ml. of water. The product is extracted with three 100 ml. portions of ethyl acetate, washed with 50 ml. of a 5% sodium hydroxide solution, 50 ml. of water and 50 ml. of saturated sodium chloride solution and dried over anhydrous magnesium sulfate. After filtering, solvents are removed at 15 - 20 mm. and 30° - 40° C. to give benzylsuccinamidomethyl L-N-carbobenzyloxy-3-(3,4-diphenylmethylenedioxyphenyl)-2-methylalanine.

E. Preparation of succinamidomethyl L-3-(3,4-dihydroxyphenyl)-2-methylalaninate hydrochloride A solution of 13.8 g. (0.0189 mole) of benzylsuccinamidomethyl L-N-carbobenzyloxy-3-(3,4-diphenylmethylenedioxyphenyl)-2-methylalanine in 130 ml. of 25% absolute ethanol-75% ethyl acetate (by volume) is hydrogenated with 5 g. of a 10% palladium-on-carbon catalyst at 20° - 25° C. and an initial pressure of 40 p.s.i. for 18 hours until hydrogen uptake ceases. After removing catalyst by filtration and concentrating to dryness under reduced pressure, the residue is dissolved in 200 ml. of a 10% absolute ethanol-90% ethyl acetate (by volume) solution and stirred with 5 ml. of a saturated sodium carbonate solution and excess solid carbonate for 2 minutes. Ten grams of anhydrous magnesium sulfate are added and after a few minutes are removed by filtration. Solvents are removed under reduced pressure, the residue is washed with 25 ml. of hexane and then 25 ml. of ethyl acetate and dried under reduced pressure. The residue is retreated with sodium carbonate as before to remove the last traces of α-methyl-3,4-dihydroxyphenylalanine and converted to the hydrochloride salt with 3 ml. of 9.6 N-ethanolic-anhydrous hydrogen chloride to give succinamidomethyl L-3-(3,4-dihydroxyphenyl)-2-methylalaninate hydrochloride.

F. Preparation of succinimidomethyl L-3-(3,4-dihydroxyphenyl)-2-methylalaninate hydrochloride hydrate A mixture of 3.95 g. (10 mmole) of succinamidomethyl L-3-(3,4-dihydroxyphenyl)-2- methylalaninate hydrochloride and 100 ml. acetyl chloride is stirred at 25° C. for 6 hours. After concentrating at 15 - 20 mm. and 35° C., the residue is dissolved in 25 ml. of 1 N hydrochloric acid and is stirred under nitrogen at 20° - 25° C. for 5 hours. After lyophilization at 0.1 - 0.3 mm. for 20 hours, the residue is treated with 50 ml. of a 10% ethanol-90% ethyl acetate (by volume) solution, 5 ml. of a saturated sodium carbonate solution and 5 g. of solid sodium carbonate. After filtration, the filtrate is dried over anhydrous magnesium sulfate, filtered and concentrated at 15 - 20 mm. and 30° - 40° C. The residue is redissolved in 25 ml. of absolute ethanol, treated with 5 ml. of a 9.6 N ethanolic-anhydrous hydrogen chloride solution and concentrated under reduced pressure to give succinimidomethyl L-3-(3,4-dihydroxyphenyl)-2-methylalaninate hydrochloride hydrate, homogeneous upon thin layer chromatography [fluorescent silica gel plate, 30% methanol-70% benzene (by volume) solvent] with an observed Rf = 0.5.

EXAMPLE 42

A. Preparation of 2-hydroxyethyl L-3-(3,4-dihydroxyphenyl)-2-methylalaninate hydrochloride A solution of 0.95 g. (4.0 mmole) of L-3-(3,4-dihydroxyphenyl)-2-methylalanine sesquihydrate and 0.51 g. (4.06 mmole) of 2-bromoethanol in 5 ml. dimethyl sulfoxide is stirred at 60° C. for 5 hours and then allowed to cool to 20° - 25° C. over 23 hours. The solution is diluted with 10 ml. distilled water and passed through a column containing 5 g. of weakly basic anion exchange resin on the base cycle. After elution with water fractions, the fractions giving a positive ferric chloride test are combined and added to a column of 3 g. of weakly acidic cation exchange resin on the acid cycle. Unreacted L-3-(3,4-dihydroxyphenyl)-2-methylalanine is eluted with distilled water until a negative ferric chloride test is obtained, the ester is then eluted with 1 N acetic acid. The ester fraction, 50 ml. (pH 3.2), is acidified to pH 2.0 with 1 N hydrochloric acid and lyophilized at 0.1 - 0.3 mm. for 20 hours to give 2-hydroxyethyl L-3-(3,4-dihydroxyphenyl)-2-methylalaninate hydrochloride.

B. Preparation of 2-acetoxyethyl L-3-(3,4-dihydroxyphenyl)-2-methylalaninate A mixture of 1.0 g. (3.4 mmole) of 2-hydroxyethyl L-3-(3,4-dihydroxyphenyl)-2-methylalaninate hydrochloride and 50 ml. acetyl chloride is stirred at 25° C. for 6 hours. After concentrating at 15 - 20 mm. and 35° C., the residue is dissolved in 25 ml. of 1 N hydrochloric acid and is stirred under nitrogen at 20° - 25° C. for 5 hours. After lyophilization at 0.1 - 0.3 mm. for 20 hours, the residue is treated with 50 ml. of a 10% ethanol-90% ethyl acetate (by volume) solution, 5 ml. of a saturated sodium carbonate solution and 5 g. of solid sodium carbonate. After filtering, the filtrate is dried over anhydrous magnesium sulfate, filtered and concentrated at 15 - 20 mm. and 30° - 40° C.

The residue is chromatographed on silica gel and eluted with 20% methanol-80% benzene (by volume). Recrystallization is accomplished by dissolving the ester in warm ethyl acetate and adding sufficient cyclohexane to precipitate the desired 2-acetoxyethyl L-3-(3,4-dihydroxyphenyl)-2-methylalaninate, m.p. 114° - 118° C. dec.

EXAMPLE 43

Preparation of 2-acetoxyethyl L-3-(3,4-dihydroxyphenyl)-2-methylalaninate

A mixture of 1.0 g. (3.4 mmole) of 2-hydroxyethyl L-3-(3,4-dihydroxyphenyl)-2-methylalaninate hydrochloride and 50 ml. methanesulfonylchloride is stirred at 25° C. for 6 hours. Concentration at 15 - 20 mm. and 35° C. followed by drying at 0.1 - 0.5 mm. and 40° C. gives the crude methanesulfonyl derivative. To this is added 10 ml. dimethylsulfoxide and 6.6 g. (10 mmole) of lithium acetate and the mixture is stirred at 60° C. for 6 hours. Following the addition of excess ethanolic-anhydrous hydrogen chloride solution, dimethylsulfoxide is removed by stirring three times with 50 ml. ethyl ether and decanting off the ethyl ether. The residue is dissolved in 25 ml. of 1 N hydrochloric acid and is stirred under nitrogen at 20° - 25° C. for 1 hour. After lyophilization at 0.1 - 0.3 mm. for 20 hours, the residue is treated with 50 ml. of a 10% ethanol-90% ethyl acetate (by volume) solution, 5 ml. of a saturated sodium carbonate solution and 5 g. of solid sodium carbonate. After filtration, the filtrate is dried over anhydrous magnesium sulfate, filtered and concentrated at 15 - 20 mm. and 30° - 40° C.

The residue is chromatographed on silica gel and eluted with 20% methanol-80% benzene (by volume). Recrystallization of the ester is accomplished by dissolving it in ethyl acetate and adding sufficient cyclohexane to precipitate the desired 2-acetoxyethyl L-3-(3,4-dihydroxyphenyl)-2-methylalaninate, m.p. 114 - 118° C. dec.

Example 44

HARD GELATIN CAPSULES

|  | Gm. |
| --- | --- |
| succinimidomethyl L-3-(3,4-dihydroxyphenyl)-2-methylalaninate hydrochloride hydrate | 200 |
| Cornstarch | 150 |
| Magnesium stearate, powder | 50 |
| Talc | 50 |

The finely powdered ingredients are mixed thoroughly and then encapsulated in 1000 two-piece hard gelatin capsules each containing 200 mgs. of succinimidomethyl L-3-(3,4-dihydroxyphenyl)-2-methylalaninate hydrochloride hydrate.

EXAMPLE 45

TABLETS

1000 Tablets each containing 100 mgs. of α-succinimidoethyl L-3-(3,4-dihydroxyphenyl)-2-methylalaninate hydrochloride dihydrate (β-isomer) are prepared from the following ingredients:

|  | Gm. |
| --- | --- |
| α-succinimidoethyl L-3-(3,4-dihydroxyphenyl)-2-methylalaninate hydrochloride dihydrate (β-isomer) | 100 |
| Lactose | 50 |
| Starch | 50 |
| Calcium stearate | 10 |
| Talc | 10 |

The finely powdered ingredients are mixed thoroughly and then tableted by a slugging procedure.

EXAMPLE 46

HARD GELATIN CAPSULES

Five thousand two-piece hard gelatin capsules, each containing 400 mg. of α-pivaloyloxyethyl L-3-(3,4-dihydroxyphenyl)-2-methylalaninate hydrochloride are prepared from the following ingredients:

|  | Gm. |
|---|---|
| α-pivaloyloxyethyl L-3-(3,4-dihydroxyphenyl)-2-methylalaninate hydrochloride | 2000 |
| Lactose | 3000 |
| Magnesium stearate | 1000 |
| Talc | 1000 |

The finely powdered ingredients are mixed thoroughly and then encapsulated by conventional techniques.

EXAMPLE 47

Anti-Hypertensive Activity

The procedure for evaluating the anti-hypertensive activity of the active agents comprises administering the compound either orally or intraperitoneally in spontaneously hypertensive rats of the Wistar-Okamoto strain. Arterial pressure is recorded continuously in these animals through an indwelling aortic catheter introduced through the caudal artery. The animals are allowed free movement in the metabolism cage during the measurements.

When the compounds of the present invention are tested orally, distinct anti-hypertensive activity is noted. The compounds also show anti-hypertensive activity when tested intraperitoneally. In some instances the compounds show substantially more activity than L-α-methyldopa.

Many other equivalent modifications will be apparent to those skilled in the art from a reading of the foregoing without a departure from the inventive concept.

What is claimed is:

1. A compound of the formula

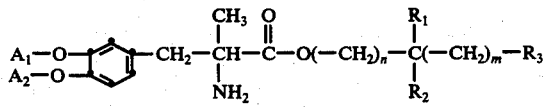

wherein $n$ is 0, 1, 2 or 3;

$m$ is 0, 1, 2 or 3;

$A_1$ and $A_2$ are individually H or a lower alkanoyl group;

$R_1$ and $R_2$ are individually H or alkyl of 1 to 3 carbon atoms and;

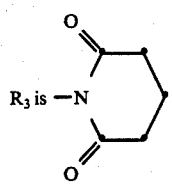

or a pharmaceutically acceptable acid addition salt thereof.

2. A free base of the compound of claim 1.

3. A pharmaceutically acceptable acid addition salt of the compound of claim 1.

4. An ester of the L isomer of an amino acid, substantially free of the D isomer, having the formula

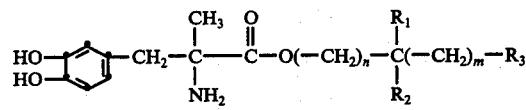

wherein $n$ is 0, 1, 2 or 3;

$m$ is 0, 1, 2 or 3;

$R_1$ and $R_2$ are individually H or alkyl of 1 to 3 carbon atoms and;

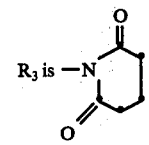

or a pharmaceutically acceptable acid addition salt thereof.

5. A free base of the ester of claim 4.

6. A pharmaceutically acceptable acid addition salt of the ester of claim 4.

7. The compounds of claim 1 wherein said

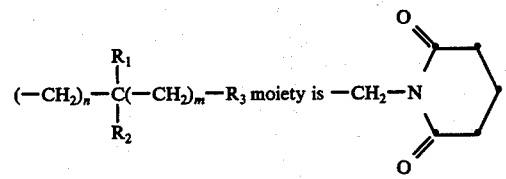

8. The hydrochloric acid addition salt of claim 7.

9. The compound of claim 4 wherein

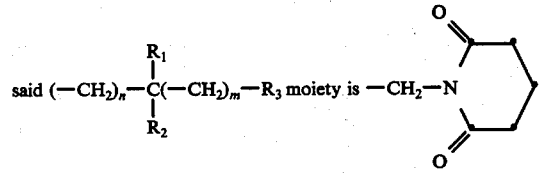

10. The hydrochloric acid addition salt of claim 9.

* * * * *